(12) United States Patent
Stransky et al.

(10) Patent No.: US 10,407,509 B2
(45) Date of Patent: Sep. 10, 2019

(54) NTRK2 FUSIONS

(71) Applicant: Blueprint Medicines Corporation, Cambridge, MA (US)

(72) Inventors: Nicolas Stransky, Charlestown, MA (US); Ethan G. Cerami, Winchester, MA (US); Christoph Lengauer, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 14/909,040

(22) PCT Filed: Jul. 30, 2014

(86) PCT No.: PCT/US2014/048881
§ 371 (c)(1),
(2) Date: Jan. 29, 2016

(87) PCT Pub. No.: WO2015/017533
PCT Pub. Date: Feb. 5, 2015

(65) Prior Publication Data
US 2016/0272725 A1    Sep. 22, 2016

Related U.S. Application Data

(60) Provisional application No. 61/943,028, filed on Feb. 21, 2014, provisional application No. 61/860,153, filed on Jul. 30, 2013.

(51) Int. Cl.
| | | |
|---|---|---|
| *C07K 16/40* | (2006.01) | |
| *C12Q 1/6886* | (2018.01) | |
| *C12Q 1/48* | (2006.01) | |
| *G01N 33/574* | (2006.01) | |
| *C07K 16/28* | (2006.01) | |
| *C07K 16/30* | (2006.01) | |
| *C12N 15/113* | (2010.01) | |

(52) U.S. Cl.
CPC .......... *C07K 16/40* (2013.01); *C07K 16/2863* (2013.01); *C07K 16/30* (2013.01); *C12N 15/1137* (2013.01); *C12Q 1/485* (2013.01); *C12Q 1/6886* (2013.01); *G01N 33/57484* (2013.01); *G01N 33/57492* (2013.01); *C07K 2317/34* (2013.01); *C07K 2317/76* (2013.01); *C12N 2320/30* (2013.01); *C12Q 2600/112* (2013.01); *C12Q 2600/156* (2013.01); *C12Q 2600/158* (2013.01); *C12Q 2600/178* (2013.01); *G01N 2333/91205* (2013.01); *G01N 2500/04* (2013.01)

(58) Field of Classification Search
USPC .................................................... 424/139.1
See application file for complete search history.

(56) References Cited

U.S. PATENT DOCUMENTS

| | | | | |
|---|---|---|---|---|
| 2016/0101090 A1* | 4/2016 | Flynn | ..................... | A61K 31/44 514/349 |
| 2016/0137654 A1* | 5/2016 | Arrigo | ................. | C07D 487/04 514/259.31 |
| 2016/0153039 A1* | 6/2016 | Amorese | .............. | C12Q 1/6874 506/2 |
| 2016/0251446 A1 | 9/2016 | Stransky et al. | | |
| 2017/0044621 A1 | 2/2017 | Cerami et al. | | |
| 2017/0044622 A1 | 2/2017 | Cerami et al. | | |
| 2017/0114417 A1 | 4/2017 | Stransky et al. | | |
| 2017/0137889 A1 | 5/2017 | Stransky et al. | | |
| 2017/0165267 A1* | 6/2017 | Arrigo | ................. | A61K 31/519 |
| 2017/0198356 A1 | 7/2017 | Stransky | | |
| 2017/0211148 A1 | 7/2017 | Stransky et al. | | |
| 2017/0211149 A1 | 7/2017 | Stransky et al. | | |
| 2017/0356052 A1 | 12/2017 | Stransky | | |

FOREIGN PATENT DOCUMENTS

| | | | |
|---|---|---|---|
| WO | WO 2006/123113 | A2 | 11/2006 |
| WO | WO 2008/008310 | A2 | 1/2008 |
| WO | WO 2008/061370 | A1 | 5/2008 |
| WO | WO 2009/140128 | A2 | 11/2009 |
| WO | WO 2011/006074 | A1 | 1/2011 |
| WO | WO 2011/087709 | A2 | 7/2011 |
| WO | WO 2011/133637 | A2 | 10/2011 |
| WO | WO 2012/034091 | A1 | 3/2012 |
| WO | WO 2012/034095 | A1 | 3/2012 |
| WO | WO 2012/116217 | A1 | 8/2012 |
| WO | WO 2013/074518 | A1 | 5/2013 |

(Continued)

OTHER PUBLICATIONS

Lin et al. (Neuro-Oncology, (Jun. 2016) vol. 18, Supp. Supplement 3, pp. iii58. Abstract No. HG-48. Meeting Info: 17th International Symposium on Pediatric Neuro-Oncology ISPNO 2016. Liverpool, United Kingdom. Jun. 12, 2016-Jun. 15, 2016).*
Amgen vs Sanofi and Regeron (Case: 17-1480 Document: 176 Filed: Feb. 6, 2018).*
Albaugh, Pam, et al., "Discovery of GNF-5837, a Selective TRK Inhibitor with Efficacy in Rodent Cancer Tumor Models," *ACS Medical Chemistry Letters*, vol. 3, No. 2, Feb. 1, 2012, 140-145.
Cazoria, Maxime, et al., "Identification of a low-molecular weight TrkB antagonist with anxiolytic and antidepressant activity in mice," *Journal of Clinical Investigation*, vol. 121, No. 5, May 2, 2011, 1846-1857.
Douma, Sirith, et al., "Suppression of anoikis and induction of metastasis by the neurotrophic receptor TrkB," *Nature*, vol. 430, No. 7003, Aug. 26, 2004, 1034-1039.

(Continued)

*Primary Examiner* — Lynn A Bristol
(74) *Attorney, Agent, or Firm* — Finnegan, Henderson, Farabow, Garrett & Dunner LLP

(57) ABSTRACT

The invention provides to NTRK ("Neurotrophic Tyrosine Receptor Kinase) gene fusions, NTRK, fusion proteins, and fragments of those genes and polypeptides. The invention further provides methods of diagnosing and treating diseases or disorders associated with NTRK fusions, such as conditions mediated by aberrant NTRK expression or activity, or overexpression of NTRK.

8 Claims, 8 Drawing Sheets

Specification includes a Sequence Listing.

(56) References Cited

FOREIGN PATENT DOCUMENTS

WO      WO 2013/174876 A1      11/2013

OTHER PUBLICATIONS

Huang, Yet Ta, et al., "TrkB antibody elicits cytotoxicity and suppresses migration/invasion of transitional cell carcinoma cells," *International Journal of Oncology*, vol. 37, 2010, 943-949.

International Search Report and Written Opinion of International Application No. PCT/US2014/048881, dated Dec. 15, 2014 (21 pages).

Jones, David T.W., et al., "Recurrent somatic alterations of FGFR1 and NTRK2 in pilocytic astrocytoma," *Nature Genetics*, vol. 45, No. 8, Jun. 30, 2013, 927-932.

Ryan, J., et al., "MicroRNA-204 increases sensitivity of neuroblastoma cells to cisplatin and is associated with a favourable clinical outcome," *British Journal of Cancer*, vol. 107, No. 6, Aug. 14, 2012, 967-976.

Soda, M., et al., "Identification of the transforming EML4-ALK fusion gene in non-small-cell lung cancer," *Nature*, vol. 448, Aug. 2007, 561-566.

Stransky, et al., "The landscape of kinase fusions in cancer," *Nature Communications*, vol. 5, Sep. 10, 2014, retrieved on Dec. 3, 2014 from URL:http://www.nature.com/ncomms/2014/140910/ncomms5846/extref/ncomms5846-s3.xlsx.

Thiele, Carol J., et al., "On Trk—The TrkB Signal Transduction Pathway is an Increasingly Important Target in Cancer Biology," *Clinical Cancer Research*, vol. 15, No. 19, Sep. 15, 2009, 5962-5967.

Youn, Ahrim, "Identifying cancer driver genes in tumor genome sequencing studies," *Bioinformatics*, vol. 27, No. 2, Dec. 17, 2010, 175-181.

Stransky, N. et al. (2014) "The landscape of kinase fusions in cancer" *Nature Communications*, 5:4846.

Amatu, A. et al. (2016) "NTRK gene fusions as novel targets of cancer therapy across multiple tumour types" *ESMO Open*, 1.2:e000023.

Vaishnavi, A. et al (2014) "TRKing Down an Old Oncogene in a New Era of Targeted Therapy" *Cancer Discovery*, 5.1: 25-34.

\* cited by examiner

FIGURE 1

ATGGAGGTGG CGGTGGAGAA GGCGGTGGCG GCGGCGGCAG CGGCCTCGGC TGCGGCCTCC GGGGGGCCCT
CGGCGGCGCC GAGCGGGGAG AACGAGGCCG AGAGTCGGCA GGGCCCGGAC TCGGAGCGCG GCGGCGAGGC
GGCCCGGCTC AACCTGTTGG ACACTTGCGC CGTGTGCCAC CAGAACATCC AGAGCCGGGC GCCCAAGCTG
CTGCCCTGCC TGCACTCTTT CTGCCAGCGC TGCCTGCCCG CGCCCCAGCG CTACCTCATG CTGCCCGCGC
CCATGCTGGG CTCGGCCGAG ACCCCGCCAC CCGTCCCTGC CCCCGGCTCG CCGGTCAGCG GCTCGTCGCC
GTTCGCCACC CAAGTTGGAG TCATTCGTTG CCCAGTTTGC AGCCAAGAAT GTGCAGAGAG ACACATCATA
GATAACTTTT TTGTGAAGGA CACTACTGAG GTTCCAGCA GTACAGTAGA AAAGTCAAAT CAGGTATGTA
CAAGCTGTGA GGACAACGCA GAAGCCAATG GGTTTTGTGT AGAGTGTGTT GAATGGCTCT GCAAGACGTG
TATCAGAGCT CATCAGAGGG TAAAGTTCAC AAAAGACCAC ACTGTCAGAC AGAAAGAGGA AGTATCTCCA
GAGGCAGTTG GTGTCACCAG CCAGCGACCA GTGTTTTGTC CTTTTCATAA AAAGGAGCAG CTGAAGCTGT
ACTGTGAGAC ATGTGACAAA CTGACATGTC GAGACTGTCA GTTGTTAGAA CATAAAGAGC ATAGATACCA
ATTTATAGAA GAAGCTTTTC AGAATCAGAA AGTGATCATA GATACACTAA TCACCAAACT GATGGAAAAA
ACAAAATACA TAAAATTCAC AGGAAATCAG ATCCAAAACA GAATTATTGA AGTAAATCAA AATCAAAAGC
AGGTGGAACA GGATATTAAA GTTGCTATAT TTACACTGAT GGTAGAAATA AATAAAAAAG GAAAAGCTCT
ACTGCATCAG TTAGAGAGCC TTGCAAAGGA CCATCGCATG AAACTTATGC AACAACAACA GGAAGTGGCT
GGACTCTCTA AACAATTGGA GCATGTCATG CATTTTTCTA AATGGGCAGT TTCCAGTGGC AGCAGTACAG
CATTACTTTA TAGCAAACGA CTGATTACAT ACCGGTTACG GCACCTCCTT CGTGCAAGGT GTGATGCATC
CCCAGTGACC AACAACACCA TCCAATTTCA CTGTGATCCT AGTTCTGGG CTCAAAATAT CATCAACTTA
GGTTCTTTAG TAATCGAGGA TAAAGAGAGC CAGCCACAAA TGCCTAAGCA GAATCCTGTC GTGGAACAGA
ATTCACAGCC ACCAAGTGGT TTATCATCAA ACCAGTTATC CAAGTTCCCA ACACAGATCA GCCTAGCTCA
ATTACGGCTC CAGCATATGC AGCAACAGGT AATGGCTCAG AGGCAACAGG TGCAACGGAG GCCAGCACCT
GTGGGTTTAC CAAACCCTAG AATGCAGGGG CCCATCCAGC AACCTTCCAT CTCTCATCAG CAACCGCCTC
CACGTTTGAT AAACTTTCAG AATCACAGCC CCAAACCCAA TGGACCAGTT CTTCCTCCTC ATCCTCAACA
ACTGAGATAT CCACCAAACC AGAACATACC ACGACAAGCA ATAAAGCCAA ACCCCCTACA GATGGCTTTC
TTGGCTCAAC AAGCCATAAA ACAGTGGCAG ATCAGCAGTG GACAGGGAAC CCCATCAACT ACCAACAGCA
CATCCTCTAC TCCTTCCAGC CCCACGATTA CTAGTGCAGC AGGATATGAT GGAAAGGCTT TTGGTTCACC
TATGATCGAT TTGAGCTCAC CAGTGGGAGG GTCTTATAAT CTTCCCTCTC TTCCGGATAT TGACTGTTCA
AGTACTATTA TGCTGGACAA TATTGTGAGG AAAGATACTA ATATAGATCA TGGCCAGCCA AGACCACCCT
CAAACAGAAC GGTCCAGTCA CCAAATTCAT CAGTGCCATC TCCAGGCCTT GCAG/GCCAG CCTCCGTTAT
CAGCAATGAT GATGACTCTG CCAGCCCACT CCATCACATC TCCAATGGGA GTAACACTCC ATCTTCTTCG
GAAGGTGGCC CAGATGCTGT CATTATTGGA ATGACCAAGA TCCCTGTCAT TGAAAATCCC CAGTACTTTG
GCATCACCAA CAGTCAGCTC AAGCCAGACA CATTTGTTCA GCACATCAAG CGACATAACA TTGTTCTGAA
AAGGGAGCTA GGCGAAGGAG CCTTTGGAAA AGTGTTCCTA GCTGAATGCT ATAACCTCTG TCCTGAGCAG
GACAAGATCT TGGTGGCAGT GAAGACCCTG AAGGATGCCA GTGACAATGC ACGCAAGGAC TTCCACCGTG
AGGCCGAGCT CCTGACCAAC CTCCAGCATG AGCACATCGT CAAGTTCTAT GGCGTCTGCG TGGAGGGCGA
CCCCCTCATC ATGGTCTTTG AGTACATGAA GCATGGGGAC CTCAACAAGT TCCTCAGGGC ACACGGCCCT
GATGCCGTGC TGATGGCTGA GGGCAACCCG CCCACGGAAC TGACGCAGTC GCAGATGCTG CATATAGCCC
AGCAGATCGC CGCGGGCATG GTCTACCTGG CGTCCCAGCA CTTCGTGCAC CGCGATTTGG CCACCAGGAA
CTGCCTGGTC GGGGAGAACT TGCTGGTGAA AATCGGGGAC TTTGGGATGT CCCGGGACGT GTACAGCACT
GACTACTACA GGGTCGGTGG CCACACAATG CTGCCCATTC GCTGGATGCC TCCAGAGAGC ATCATGTACA
GGAAATTCAC GACGGAAAGC GACGTCTGGA GCCTGGGGGT CGTGTTGTGG GAGATTTTCA CCTATGGCAA
ACAGCCCTGG TACCAGCTGT CAAACAATGA GGTGATAGAG TGTATCACTC AGGGCCGAGT CCTGCAGCGA
CCCCGCACGT GCCCCCAGGA GGTGTATGAG CTGATGCTGG GGTGCTGGCA GCGAGAGCCC CACATGAGGA
AGAACATCAA GGGCATCCAT ACCCTCCTTC AGAACTTGGC CAAGGCATCT CCGGTCTACC TGGACATTCT
AGGCTAG (SEQ ID NO:1)

FIGURE 2

ATGGAGGTGG CGGTGGAGAA GGCGGTGGCG GCGGCGGCAG CGGCCTCGGC TGCGGCCTCC
GGGGGGCCCT CGGCGGCGCC AACGAGGCCG AGAGTCGGCA GGGCCCGGAC TCGGAGCGCG
GCGGCGAGGC GGCCCGGCTC AACCTGTTGG ACACTTGCGC CGTGTGCCAC CAGAACATCC
AGAGCCGGGC GCCCAAGCTG CTGCCCTGCC TGCACTCTTT CTGCCAGCGC TGCCTGCCCG
CGCCCCAGCG CTACCTCATG CTGCCCGCGC CCATGCTGGG CTCGGCCGAG ACCCCGCCAC
CCGTCCCTGC CCCCGGCTCG CCGGTCAGCG GCTCGTCGCC GTTCGCCACC CAAGTTGGAG
TCATTCGTTG CCCAGTTTGC AGCCAAGAAT GTGCAGAGAG ACACATCATA GATAACTTTT
TTGTGAAGGA CACTACTGAG GTTCCCAGCA GTACAGTAGA AAAGTCAAAT CAGGTATGTA
CAAGCTGTGA GGACAACGCA GAAGCCAATG GGTTTTGTGT AGAGTGTGTT GAATGGCTCT
GCAAGACGTG TATCAGAGCT CATCAGAGGG TAAAGTTCAC AAAAGACCAC ACTGTCAGAC
AGAAAGAGGA AGTATCTCCA GAGGCAGTTG GTGTCACCAG CCAGCGACCA GTGTTTTGTC
CTTTTCATAA AAAGGAGCAG CTGAAGCTGT ACTGTGAGAC ATGTGACAAA CTGACATGTC
GAGACTGTCA GTTGTTAGAA CATAAAGAGC ATAGATACCA ATTTATAGAA GAAGCTTTTC
AGAATCAGAA AGTGATCATA GATACACTAA TCACCAAACT GATGGAAAAA ACAAAATACA
TAAAATTCAC AGGAAATCAG ATCCAAAACA GAATTATTGA AGTAAATCAA AATCAAAAGC
AGGTGGAACA GGATATTAAA GTTGCTATAT TTACACTGAT GGTAGAAATA AATAAAAAAG
GAAAAGCTCT ACTGCATCAG TTAGAGAGCC TTGCAAAGGA CCATCGCATG AAACTTATGC
AACAACAACA GGAAGTGGCT GGACTCTCTA AACAATTGGA GCATGTCATG CATTTTTCTA
AATGGGCAGT TTCCAGTGGC AGCAGTACAG CATTACTTTA TAGCAAACGA CTGATTACAT
ACCGGTTACG GCACCTCCTT CGTGCAAGGT GTGATGCATC CCCAGTGACC AACAACACCA
TCCAATTTCA CTGTGATCCT AGTTTCTGGG CTCAAAATAT CATCAACTTA GGTTCTTTAG
TAATCGAGGA TAAAGAGAGC CAGCCACAAA TGCCTAAGCA GAATCCTGTC GTGGAACAGA
ATTCACAGCC ACCAAGTGGT TTATCATCAA ACCAGTTATC CAAGTTCCCA ACACAGATCA
GCCTAGCTCA ATTACGGCTC CAGCATATGC AGCAACAGGT AATGGCTCAG AGGCAACAGG
TGCAACGGAG GCCAGCACCT GTGGGTTTAC CAAACCCTAG AATGCAGGGG CCCATCCAGC
AACCTTCCAT CTCTCATCAG CAACCGCCTC CACGTTTGAT AAACTTTCAG AATCACAGCC
CCAAACCCAA TGGACCAGTT CTTCCTCCTC ATCCTCAACA ACTGAGATAT CCACCAAACC
AGAACATACC ACGACAAGCA ATAAAGCCAA ACCCCCTACA GATGGCTTTC TTGGCTCAAC
AAGCCATAAA ACAGTGGCAG ATCAGCAGTG GACAGGGAAC CCCATCAACT ACCAACAGCA
CATCCTCTAC TCCTTCCAGC CCCACGATTA CTAGTGCAGC AGGATATGAT GGAAAGGCTT
TTGGTTCACC TATGATCGAT TTGAGCTCAC CAGTGGGAGG GTCTTATAAT CTTCCCTCTC
TTCCGGATAT TGACTGTTCA AGTACTATTA TGCTGGACAA TATTGTGAGG AAAGATACTA
ATATAGATCA TGGCCAGCCA AGACCACCCT CAAACAGAAC GGTCCAGTCA CCAAATTCAT
CAGTGCCATC TCCAGGCCTT GCAG/ATTTCT CATGGTTTGG ATTTGGGAAA GTAAAATCAA
GACAAGGTGT TGGCCCAGCC TCCGTTATCA GCAATGATGA TGACTCTGCC AGCCCACTCC
ATCACATCTC CAATGGGAGT AACACTCCAT CTTCTTCGGA AGGTGGCCCA GATGCTGTCA
TTATTGGAAT GACCAAGATC CCTGTCATTG AAAATCCCCA GTACTTTGGC ATCACCAACA
GTCAGCTCAA GCCAGACACA TTTGTTCAGC ACATCAAGCG ACATAACATT GTTCTGAAAA
GGGAGCTAGG CGAAGGAGCC TTTGGAAAAG TGTTCCTAGC TGAATGCTAT AACCTCTGTC
CTGAGCAGGA CAAGATCTTG GTGGCAGTGA AGACCCTGAA GGATGCCAGT GACAATGCAC
GCAAGGACTT CCACCGTGAG GCCGAGCTCC TGACCAACCT CCAGCATGAG CACATCGTCA
AGTTCTATGG CGTCTGCGTG GAGGGCGACC CCCTCATCAT GGTCTTTGAG TACATGAAGC
ATGGGGACCT CAACAAGTTC CTCAGGGCAC ACGGCCCTGA TGCCGTGCTG ATGGCTGAGG
GCAACCCGCC CACGGAACTG ACGCAGTCGC AGATGCTGCA TATAGCCCAG CAGATCGCCG
CGGGCATGGT CTACCTGGCG TCCCAGCACT TCGTGCACCG CGATTTGGCC ACCAGGAACT
GCCTGGTCGG GGAGAACTTG CTGGTGAAAA TCGGGGACTT TGGGATGTCC CGGGACGTGT
ACAGCACTGA CTACTACAGG GTCGGTGGCC ACACAATGCT GCCCATTCGC TGGATGCCTC
CAGAGAGCAT CATGTACAGG AAATTCACGA CGGAAAGCGA CGTCTGGAGC CTGGGGGTCG
TGTTGTGGGA GATTTTCACC TATGGCAAAC AGCCCTGGTA CCAGCTGTCA AACAATGAGG
TGATAGAGTG TATCACTCAG GGCCGAGTCC TGCAGCGACC CCGCACGTGC CCCCAGGAGG
TGTATGAGCT GATGCTGGGG TGCTGGCAGC GAGAGCCCCA CATGAGGAAG AACATCAAGG
GCATCCATAC CCTCCTTCAG AACTTGGCCA AGGCATCTCC GGTCTACCTG GACATTCTAG
GCTAG (SEQ ID NO:2)

FIGURE 3

MEVAVEKAVA AAAAASAAAS GGPSAAPSGE NEAESRQGPD SERGGEAARL NLLDTCAVCH QNIQSRAPKL
LPCLHSFCQR CLPAPQRYLM LPAPMLGSAE TPPPVPAPGS PVSGSSPFAT QVGVIRCPVC SQECAERHII
DNFFVKDTTE VPSSTVEKSN QVCTSCEDNA EANGFCVECV EWLCKTCIRA HQRVKFTKDH TVRQKEEVSP
EAVGVTSQRP VFCPFHKKEQ LKLYCETCDK LTCRDCQLLE HKEHRYQFIE EAFQNQKVII DTLITKLMEK
TKYIKFTGNQ IQNRIIEVNQ NQKQVEQDIK VAIFTLMVEI NKKGKALLHQ LESLAKDHRM KLMQQQQEVA
GLSKQLEHVM HFSKWAVSSG SSTALLYSKR LITYRLRHLL RARCDASPVT NNTIQFHCDP SFWAQNIINL
GSLVIEDKES QPQMPKQNPV VEQNSQPPSG LSSNQLSKFP TQISLAQLRL QHMQQQVMAQ RQQVQRRPAP
VGLPNPRMQG PIQQPSISHQ QPPPRLINFQ NHSPKPNGPV LPPHPQQLRY PPNQNIPRQA IKPNPLQMAF
LAQQAIKQWQ ISSGQGTPST TNSTSSTPSS PTITSAAGYD GKAFGSPMID LSSPVGGSYN LPSLPDIDCS
STIMLDNIVR KDTNIDHGQP RPPSNRTVQS PNSSVPSPGL AGPASVISND DDSASPLHHI SNGSNTPSSS
EGGPDAVIIG MTKIPVIENP QYFGITNSQL KPDTFVQHIK RHNIVLKREL GEGAFGKVFL AECYNLCPEQ
DKILVAVKTL KDASDNARKD FHREAELLTN LQHEHIVKFY GVCVEGDPLI MVFEYMKHGD LNKFLRAHGP
DAVLMAEGNP PTELTQSQML HIAQQIAAGM VYLASQHFVH RDLATRNCLV GENLLVKIGD FGMSRDVYST
DYYRVGGHTM LPIRWMPPES IMYRKFTTES DVWSLGVVLW EIFTYGKQPW YQLSNNEVIE CITQGRVLQR
PRTCPQEVYE LMLGCWQREP HMRKNIKGIH TLLQNLAKAS PVYLDILG    (SEQ ID NO:3)

FIGURE 4

```
MEVAVEKAVA AAAAASAAAS GGPSAAPSGE NEAESRQGPD SERGGEAARL NLLDTCAVCH QNIQSRAPKL
LPCLHSFCQR CLPAPQRYLM LPAPMLGSAE TPPPVPAPGS PVSGSSPFAT QVGVIRCPVC SQECAERHII
DNFFVKDTTE VPSSTVEKSN QVCTSCEDNA EANGFCVECV EWLCKTCIRA HQRVKFTKDH TVRQKEEVSP
EAVGVTSQRP VFCPFHKKEQ LKLYCETCDK LTCRDCQLLE HKEHRYQFIE EAFQNQKVII DTLITKLMEK
TKYIKFTGNQ IQNRIIEVNQ NQKQVEQDIK VAIFTLMVEI NKKGKALLHQ LESLAKDHRM KLMQQQQEVA
GLSKQLEHVM HFSKWAVSSG SSTALLYSKR LITYRLRHLL RARCDASPVT NNTIQFHCDP SFWAQNIINL
GSLVIEDKES QPQMPKQNPV VEQNSQPPSG LSSNQLSKFP TQISLAQLRL QHMQQQVMAQ RQQVQRRPAP
VGLPNPRMQG PIQQPSISHQ QPPPRLINFQ NHSPKPNGPV LPPHPQQLRY PPNQNIPRQA IKPNPLQMAF
LAQQAIKQWQ ISSGQGTPST TNSTSSTPSS PTITSAAGYD GKAFGSPMID LSSPVGGSYN LPSLPDIDCS
STIMLDNIVR KDTNIDHGQP RPPSNRTVQS PNSSVPSPGL ADFSWFGFGK VKSRQGVGPA SVISNDDDSA
SPLHHISNGS NTPSSSEGGP DAVIIGMTKI PVIENPQYFG ITNSQLKPDT FVQHIKRHNI VLKRELGEGA
FGKVFLAECY NLCPEQDKIL VAVKTLKDAS DNARKDFHRE AELLTNLQHE HIVKFYGVCV EGDPLIMVFE
YMKHGDLNKF LRAHGPDAVL MAEGNPPTEL TQSQMLHIAQ QIAAGMVYLA SQHFVHRDLA TRNCLVGENL
LVKIGDFGMS RDVYSTDYYR VGGHTMLPIR WMPPESIMYR KFTTESDVWS LGVVLWEIFT YGKQPWYQLS
NNEVIECITQ GRVLQRPRTC PQEVYELMLG CWQREPHMRK NIKGIHTLLQ NLAKASPVYL DILG
(SEQ ID NO:4)
```

FIGURE 5

ATGGAAGAGT TAATAGTTGA ACTTCGTCTC TTTCTTGAAC TCCTGGACCA TGAATATCTA ACCTCAACTG
TCAGGGAGAA AAAGGCAGTG ATAACCAACA TTCTGCTAAG AATACAGTCA TCCAAAGGTT TTGATGTGAA
GGACCATGCT CAGAAGCAGG AGACCGCTAA CAGCCTGCCA GCCCCTCCTC AGATGCCCCT GCCGGAGATC
CCTCAGCCCT GGCTGCCTCC TGACAGTGGG CCTCCACCAT TGCCAACATC CTCCCTCCCA GAAGGTTATT
ATGAGGAAGC TGTGCCGCTG AGCCCCGGAA AAGCTCCGGA ATACATCACA TCAAATTATG ATTCCGATGC
GATGAGCAGC TCTTATGAGT CGTATGATGA AGAGGAGGAG GATGGGAAGG GGAAGAAAAC CCGGCACCAG
TGGCCCTCCG AGGAGGCCTC CATGGACCTG GTCAAGGACG CCAAAATCTG CGCCTTCCTG CTGCGGAAGA
AGCGGTTCGG CCAGTGGACC AAGTTGCTCT GCGTCATCAA AGACACCAAA CTGCTGTGCT ATAAAAGTTC
CAAGGACCAG CAGCCTCAGA TGGAACTGCC ACTCCAAGGC TGTAACATTA CGTACATCCC GAAAGACAGC
AAAAAGAAGA AGCACGAGCT GAAGATTACT CAGCAGGGCA CGGACCCGCT TGTTCTCGCC GTCCAGAGCA
AGGAACAGGC CGAGCAGTGG CTGAAGGTGA TCAAAGAAGC CTACAGTGGT TGTAGTGGCC CCGTGGATTC
AGAGTGTCCT CCTCCACCAA GCTCCCCGGT GCACAAGGCA GAACTGGAGA AGAAACTGTC TTCAGAGAGA
CCCAGCTCAG ATGGGGAGGG TGTTGTGGAA AATGGAATTA CCACATGTAA TGGAAAGGAG CAAGTGAAGA
GGAAGAAAAG TTCCAAATCA GAGGCCAAGG GCACTGTGTC GAAAGTCACT GGGAAAAAAA TCACCAAGAT
CATCAGTCTG GGAAAGAAAA AGCCGTCCAC AGACGAGCAG ACCTCCTCAG CTGAGGAAGA TGTTCCCACC
TGCGGCTATC TGAACGTGCT CTCCAACAGC CGCTGGCGAG AGCGCTGGTG CCGAGTGAAA GATAACAAGC
TCATTTTCCA CAAGGACAGG ACCGACCTGA AGACCCATAT TGTGTCTATT CCGCTCCGTG GCTGCGAGGT
GATCCCGGGT TTGGATTCTA AACATCCTCT GACGTTCCGG CTGCTGCGCA ACGGCCAGGA GGTTGCAGTA
TTGGAGGCAT CTTCTTCTGA AGACATGGGC AGGTGGATTG GGATTTTACT CGCAGAGACG GGATCGTCCA
CAGACCCGGA GGCTCTGCAC TATGACTACA TTGATGTGGA GATGTCTGCA AGTGTCATTC AGACAGCCAA
ACAGACCTTC TGTTTCATGA ACAGGCGTGT TATATCTGCT AACCCATATC TAGGGGGCAC CTCCAACGGC
TATGCCCACC CCAGCGGGAC GGCACTTCAT TATGACGATG TCCCGTGCAT CAACGGCTCG CTCAAGGGTA
AAAAGCCCCC CGTGGCGTCT AATGGGGTCA CAGGAAAAGG GAAGACTCTG AGCAGTCAGC CAAAGAAAGC
GGATCCCGCG GCTGTTGTGA AAAGGACGGG TTCGA/GTGCA AACCCAAATT ATCCTGATGT AATTTATGAA
GATTATGGAA CTGCAGCGAA TGACATCGGG GACACCACGA ACAGAAGTAA TGAAATCCCT TCCACAGACG
TCACTGATAA AACCGGTCGG GAACATCTCT CGGTCTATGC TGTGGTGGTG ATTGCGTCTG TGGTGGGATT
TTGCCTTTTG GTAATGCTGT TTCTGCTTAA GTTGGCAAGA CACTCCAAGT TTGGCATGAA AGATTTCTCA
TGGTTTGGAT TTGGGAAAGT AAAATCAAGA CAAGGTGTTG GCCCAGCCTC CGTTATCAGC AATGATGATG
ACTCTGCCAG CCCACTCCAT CACATCTCCA ATGGGAGTAA CACTCCATCT TCTTCGGAAG GTGGCCCAGA
TGCTGTCATT ATTGGAATGA CCAAGATCCC TGTCATTGAA AATCCCCAGT ACTTTGGCAT CACCAACAGT
CAGCTCAAGC CAGACACATT TGTTCAGCAC ATCAAGCGAC ATAACATTGT TCTGAAAAGG GAGCTAGGCG
AAGGAGCCTT TGGAAAAGTG TTCCTAGCTG AATGCTATAA CCTCTGTCCT GAGCAGGACA AGATCTTGGT
GGCAGTGAAG ACCCTGAAGG ATGCCAGTGA CAATGCACGC AAGGACTTCC ACCGTGAGGC CGAGCTCCTG
ACCAACCTCC AGCATGAGCA CATCGTCAAG TTCTATGGCG TCTGCGTGGA GGGCGACCCC CTCATCATGG
TCTTTGAGTA CATGAAGCAT GGGGACCTCA ACAAGTTCCT CAGGGCACAC GGCCCTGATG CCGTGCTGAT
GGCTGAGGGC AACCCGCCCA CGGAACTGAC GCAGTCGCAG ATGCTGCATA TAGCCCAGCA GATCGCCGCG
GGCATGGTCT ACCTGGCGTC CCAGCACTTC GTGCACCGCG ATTTGGCCAC CAGGAACTGC CTGGTCGGGG
AGAACTTGCT GGTGAAAATC GGGGACTTTG GGATGTCCCG GGACGTGTAC AGCACTGACT ACTACAGGGT
CGGTGGCCAC ACAATGCTGC CCATTCGCTG GATGCCTCCA GAGAGCATCA TGTACAGGAA ATTCACGACG
GAAAGCGACG TCTGGAGCCT GGGGGTCGTG TTGTGGGAGA TTTTCACCTA TGGCAAACAG CCCTGGTACC
AGCTGTCAAA CAATGAGGTG ATAGAGTGTA TCACTCAGGG CCGAGTCCTG CAGCGACCCC GCACGTGCCC
CCAGGAGGTG TATGAGCTGA TGCTGGGGTG CTGGCAGCGA GAGCCCCACA TGAGGAAGAA CATCAAGGGC
ATCCATACCC TCCTTCAGAA CTTGGCCAAG GCATCTCCGG TCTACCTGGA CATTCTAGGC
TAG (SEQ ID NO:5)

FIGURE 6

MEELIVELRL FLELLDHEYL TSTVREKKAV ITNILLRIQS SKGFDVKDHA QKQETANSLP APPQMPLPEI
PQPWLPPDSG PPPLPTSSLP EGYYEEAVPL SPGKAPEYIT SNYDSDAMSS SYESYDEEEE DGKGKKTRHQ
WPSEEASMDL VKDAKICAFL LRKKRFGQWT KLLCVIKDTK LLCYKSSKDQ QPQMELPLQG CNITYIPKDS
KKKKHELKIT QQGTDPLVLA VQSKEQAEQW LKVIKEAYSG CSGPVDSECP PPPSSPVHKA ELEKKLSSER
PSSDGEGVVE NGITTCNGKE QVKRKKSSKS EAKGTVSKVT GKKITKIISL GKKKPSTDEQ TSSAEEDVPT
CGYLNVLSNS RWRERWCRVK DNKLIFHKDR TDLKTHIVSI PLRGCEVIPG LDSKHPLTFR LLRNGQEVAV
LEASSSEDMG RWIGILLAET GSSTDPEALH YDYIDVEMSA SVIQTAKQTF CFMNRRVISA NPYLGGTSNG
YAHPSGTALH YDDVPCINGS LKGKKPPVAS NGVTGKGKTL SSQPKKADPA AVVKRTGSSA NPNYPDVIYE
DYGTAANDIG DTTNRSNEIP STDVTDKTGR EHLSVYAVVV IASVVGFCLL VMLFLLKLAR HSKFGMKDFS
WFGFGKVKSR QGVGPASVIS NDDDSASPLH HISNGSNTPS SSEGGPDAVI IGMTKIPVIE NPQYFGITNS
QLKPDTFVQH IKRHNIVLKR ELGEGAFGKV FLAECYNLCP EQDKILVAVK TLKDASDNAR KDFHREAELL
TNLQHEHIVK FYGVCVEGDP LIMVFEYMKH GDLNKFLRAH GPDAVLMAEG NPPTELTQSQ MLHIAQQIAA
GMVYLASQHF VHRDLATRNC LVGENLLVKI GDFGMSRDVY STDYYRVGGH TMLPIRWMPP ESIMYRKFTT
ESDVWSLGVV LWEIFTYGKQ PWYQLSNNEV IECITQGRVL QRPRTCPQEV YELMLGCWQR EPHMRKNIKG
IHTLLQNLAK ASPVYLDILG  (SEQ ID NO:6)

FIGURE 7

ATGAACAGTG GCGGCGGCCT CCCGCCCCCC TCGGCCGCCG CCTCCCCTTC CTCCTCCTCG CTGGCGGCGG
CGGTGGCGGT GGTGGCCCCG CCGGGGGTCG GGGGTGTCCC CGGCGGGGCG GCGGTAGGAG TGAAGCTGAA
GTACTGCCGC TACTACGCTA AGGATAAGAC TTGCTTCTAC GGGGAGGAGT GTCAGTTCCT GCATGAGGAC
CCTGCCGCCG GGGCTGCCCC GGGCCTCGGC CTCCATAGCA ACAGCGTCCC CCTGGCTCTG GCTGGTGCAC
CCGTGGCCGG CTTTCCGCCG GGAGCCGTCG CGGGCGGGGG AGCTGGGCCG CCCCCGGGC CCAAGAAGCC
GGACCTGGGG GACCCGGGGA CCGGAGCCGC AGCCGGCGGA GGAGGCAGTA GCGGGGGACT CGATGGACCG
CGGCTGGCAA/TTGTTCAGCA CATCAAGCGA CATAACATTG TTCTGAAAAG GGAGCTAGGC GAAGGAGCCT
TTGGAAAAGT GTTCCTAGCT GAATGCTATA ACCTCTGTCC TGAGCAGGAC AAGATCTTGG TGGCAGTGAA
GACCCTGAAG GATGCCAGTG ACAATGCACG CAAGGACTTC CACCGTGAGG CCGAGCTCCT GACCAACCTC
CAGCATGAGC ACATCGTCAA GTTCTATGGC GTCTGCGTGG AGGGCGACCC CCTCATCATG GTCTTTGAGT
ACATGAAGCA TGGGGACCTC AACAAGTTCC TCAGGGCACA CGGCCCTGAT GCCGTGCTGA TGGCTGAGGG
CAACCCGCCC ACGGAACTGA CGCAGTCGCA GATGCTGCAT ATAGCCCAGC AGATCGCCGC GGGCATGGTC
TACCTGGCGT CCCAGCACTT CGTGCACCGC GATTTGGCCA CCAGGAACTG CCTGGTCGGG GAGAACTTGC
TGGTGAAAAT CGGGGACTTT GGGATGTCCC GGGACGTGTA CAGCACTGAC TACTACAGGG TCGGTGGCCA
CACAATGCTG CCCATTCGCT GGATGCCTCC AGAGAGCATC ATGTACAGGA AATTCACGAC GGAAAGCGAC
GTCTGGAGCC TGGGGGTCGT GTTGTGGGAG ATTTTCACCT ATGGCAAACA GCCCTGGTAC CAGCTGTCAA
ACAATGAGGT GATAGAGTGT ATCACTCAGG GCCGAGTCCT GCAGCGACCC CGCACGTGCC CCCAGGAGGT
GTATGAGCTG ATGCTGGGGT GCTGGCAGCG AGAGCCCAC ATGAGGAAGA ACATCAAGGG CATCCATACC
CTCCTTCAGA ACTTGGCCAA GGCATCTCCG GTCTACCTGG ACATTCTAGG CTAG
                                                    (SEQ ID NO:7)

FIGURE 8

MNSGGGLPPP SAAASPSSSS LAAAVAVVAP PGVGGVPGGA AVGVKLKYCR YYAKDKTCFY GEECQFLHED
PAAGAAPGLG LHSNSVPLAL AGAPVAGFPP GAVAGGGAGP PPGPKKPDLG DPGTGAAAGG GGSSGGLDGP
RLAIVQHIKR HNIVLKRELG EGAFGKVFLA ECYNLCPEQD KILVAVKTLK DASDNARKDF HREAELLTNL
QHEHIVKFYG VCVEGDPLIM VFEYMKHGDL NKFLRAHGPD AVLMAEGNPP TELTQSQMLH IAQQIAAGMV
YLASQHFVHR DLATRNCLVG ENLLVKIGDF GMSRDVYSTD YYRVGGHTML PIRWMPPESI MYRKFTTESD
VWSLGVVLWE IFTYGKQPWY QLSNNEVIEC ITQGRVLQRP RTCPQEVYEL MLGCWQREPH MRKNIKGIHT
LLQNLAKASP VYLDILG    (SEQ ID NO:8)

NTRK2 FUSIONS

REFERENCE TO RELATED APPLICATIONS

This application is a. U.S. national stage of International Patent Application No. PCT/US2014/048881, filed Jul. 30, 2014, which claims priority to U.S. Provisional Application No. 61/860,153, filed Jul. 30, 2013, and U.S. Provisional Application No. 61/943,028, filed Feb. 21, 2014, the contents of all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 20, 2014, is named 12386.0003-00304_SL.txt and is 45,476 bytes in size.

FIELD OF THE INVENTION

This invention relates to NTRK2 (Neurotrophic Tyrosine Receptor Kinase) gene fusions and NTRK2 fusion proteins. The invention further relates to methods of diagnosing and treating diseases or disorders associated with NTRK2 fusions, such as conditions mediated by aberrant NTRK2 expression or activity, or conditions associated with overexpression of NTRK2.

BACKGROUND

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See, e.g., M. Soda et al, "Identification of the transforming EML4-ALK fusion gene in non-small-cell lung cancer," *Nature* 444:561-566 (2007).

A need exists for identifying novel genetic lesions associated with cancer. For example, the presence of fusions involving a kinase in samples collected from more than one source can indicate that the kinase is an oncogenic driver. The identification of such fusions can be an effective approach to diagnosis of cancers and development of compounds, compositions, methods, and assays for evaluating and treating cancer patients.

SUMMARY

In one aspect, the invention provides methods for detecting the presence of an NTRK2 fusion in a biological sample. The methods include the steps of: (a) obtaining a biological sample from a mammal; and (b) contacting the sample with a reagent that detects an NTRK2 fusion, to determine whether an NTRK2 fusion is present in the biological sample. In some embodiments, the sample can be from, e.g., a cancer patient, such as, e.g., a lung cancer patient, a glioma patient, or a squamous cell carcinoma patient. In some embodiments, the fusion can be, e.g., a TRIM24:NTRK2 fusion, an AFAP1:NTRK2 fusion, or a PAN3:NTRK2 fusion. In some embodiments, the TRIM24:NTRK2 fusion has all or a part of the nucleotide and/or amino acid sequence (such as, e.g., the fusion junction) set forth in SEQ ID NO:1 and SEQ ID NO:3, respectively. In some embodiments, the TRIM24:NTRK2 fusion has all or part of the nucleotide and/or amino acid sequence (such as, e.g., the fusion junction) set forth in SEQ ID NO:2 and SEQ ID NO:4, respectively. In some embodiments, the AFAP1:NTRK2 fusion has all or part of the nucleotide and/or amino acid sequence (such as, e.g., the fusion junction) set forth in SEQ ID NO:5 and SEQ ID NO:6, respectively. In some embodiments, the PAN3:NTRK2 fusion has all or part of the nucleotide and/or amino acid sequence (such as, e.g., the fusion junction) set forth in SEQ ID NO:7 and SEQ ID NO:8, respectively.

In another aspect, the invention provides methods of diagnosing a patient having a disease or disorder associated with aberrant NTRK2 expression or activity, or overexpression of NTRK2; the methods include: (a) obtaining a biological sample from the patient; and (b) contacting the sample with a reagent that detects an NTRK2 fusion to determine whether an NTRK2 fusion is present in the biological sample, wherein the detection of the NTRK2 fusion indicates the presence of a disorder associated with aberrant NTRK2 expression or activity, or overexpression of NTRK2.

The invention also includes methods of determining a therapeutic regimen for treating a cancer in a human subject; methods of identifying a patient likely to respond to treatment with an NTRK2 inhibitor or an NTRK2 fusion inhibitor; methods of stratifying a patient population by detecting an NTRK2 fusion; methods of inhibiting the proliferation of cells containing an NTRK2 fusion; methods of reducing an activity of an NTRK2 fusion; methods of treating a condition mediated by aberrant NTRK2 expression or activity; methods of treating a condition characterized by overexpression of NTRK2; methods of identifying an agent that modulates the activity of an NTRK2 fusion; and methods of monitoring disease burden in a patient having a condition mediated by NTRK2.

BRIEF DESCRIPTION OF THE FIGURES

FIG. 1 depicts the nucleotide sequence of a TRIM24:NTRK2 gene fusion (SEQ ID NO:1) comprising a portion of the TRIM24 gene (NM_015905) up to and including exon 12 (amino acid number 671) and a portion of the NTRK2 gene (NM_006180) starting at exon 16 (amino acid number 483). The underlined codons at nucleotides 2011-2013 and 2017-2019 encode the last amino acid of TRIM24 and the first amino acid of NTRK2, respectively. The slash after nucleotide 2014 indicates the breakpoint (fusion junction) where translocation and in-frame fusion has occurred. The shading at nucleotides 2014-2016 indicates that nucleotides from both TRIM24 and NTRK2 are fused in frame to form a codon and encode an amino acid.

FIG. 2 depicts the nucleotide sequence of a TRIM24: NTRK2 gene fusion (SEQ ID NO:2) comprising a portion of the TRIM24 gene (NM_015905) up to and including exon 12 (amino acid number 671) and a portion of the NTRK2 gene (NM_006180) starting at exon 15 (amino acid number 467). The underlined codons at nucleotides 2001-2003 and 2007-2009 encode the last amino acid of TRIM24 and the first amino acid of NTRK2, respectively. The slash after nucleotide 2004 indicates the breakpoint where translocation and in-frame fusion has occurred. The shading at nucleotides 2004-2006 indicates that nucleotides from both TRIM24 and NTRK2 are fused in frame to form a codon and encode an amino acid.

FIG. 3 depicts the amino acid sequence of an TRIM24: NTRK2 fusion protein (SEQ ID NO:3). The shaded amino acid at position 672 corresponds to nucleotides 2014-2016 in SEQ ID NO: 1. This amino acid is encoded by nucleotides from both TRIM24 and NTRK2.

FIG. 4 depicts the amino acid sequence of an TRIM24: NTRK2 fusion protein (SEQ ID NO:4). The shaded amino acid at position 672 corresponds to nucleotides 2004-2006 in SEQ ID NO:2. This amino acid is encoded by nucleotides from both TRIM24 and NTRK2.

FIG. 5 depicts the nucleotide sequence of an AFAP1: NTRK2 gene fusion (SEQ ID NO:5) comprising a portion of the AFAP1 gene (NM_198595) up to and including exon 13 (amino acid number 548) and a portion of the NTRK2 gene (NM_006180) starting at exon 12 (amino acid number 388). The underlined codons at nucleotides 1642-1644 and 1648-1650 encode the last amino acid of AFAP1 and the first amino acid of NTRK2, respectively. The slash after nucleotide 1645 indicates the breakpoint where translocation and in-frame fusion has occurred. The shading at nucleotides 1645-1647 indicates that nucleotides from both AFAP1 and NTRK2 are fused in frame to form a codon and encode an amino acid.

FIG. 6 depicts the amino acid sequence of an AFAP1: NTRK2 fusion protein (SEQ ID NO:6). The shaded amino acid at position 549 corresponds to nucleotides 1645-1647 of SEQ ID NO:5. This amino acid is encoded by nucleotides from both AFAP1 and NTRK2.

FIG. 7 depicts the nucleotide sequence of a PAN3: NTRK2 gene fusion (SEQ ID NO:7) comprising a portion of the PAN3 gene (NM_175854) up to exon number 1 (amino acid 143) and a portion of the NTRK2 gene (NM_006180) from exon number 17 (amino acid 546). The underlined codons at nucleotides 427-429 and 433-435 encode the last amino acid of PAN3 and the first amino acid of NTRK2, respectively. The slash after nucleotide 430 and 431 indicates the breakpoint where translocation and in-frame fusion has occurred. The shading at nucleotides 430-432 indicates that nucleotides from both PAN3 and NTRK2 are fused in frame to form a codon and encode an amino acid.

FIG. 8 depicts the amino acid sequence of a PAN3: NTRK2 fusion protein (SEQ ID NO:8). The shaded amino acid at position 144 corresponds to nucleotides 430-432 of SEQ ID NO:7. This amino acid is encoded by nucleotides from both PAN3 and NTRK2.

EXEMPLARY EMBODIMENTS OF THE INVENTION

The invention is based, at least in part, on the discovery of novel recombination or translocation events in cancer patients that result in at least a fragment of an NTRK2 gene linked to a non-homologous promoter via a recombination or translocation event that may result in aberrant expression (e.g., in a location where the kinase is not typically expressed) or overexpression of the kinase domain of the NTRK2 gene and thus, an increase in kinase activity. Thus, a new patient population is identified, which is characterized by the presence of an NTRK2 fusion, e.g., an NTRK2 gene fusion or fusion protein. This new patient population suffers from or is susceptible to disorders mediated by aberrant NTRK2 expression or activity, or overexpression of NTRK2, such as, e.g., a cancer. In another aspect of the invention, a new subtype of cancer is identified, which is characterized by the presence of the NTRK2 fusions described herein. In some embodiments, the new patient population suffers from or is susceptible to a lung cancer, glioma, or squamous cell carcinoma characterized by the presence of an NTRK2 fusion. New methods of diagnosing and treating the patient population and the NTRK2 fusion cancer subtype are also provided.

The term "NTRK2 fusion" is used generically herein, and includes any fusion molecule (e.g., gene, gene product (e.g., cDNA, mRNA, or protein), and variants thereof) that includes a fragment of NTRK2 (in the case of a nucleotide sequence, typically containing the coding region for the kinase domain of NTRK2), and a non-homologous fragment (in the case of a nucleotide sequence, the promoter and/or the coding region of a non-homologous gene, such that the coding sequence for the kinase domain of NTRK2 is under control of the promoter of the non-homologous gene). An NTRK2 fusion protein generally includes the kinase domain of NTRK2. In some embodiments, the NTRK2 fusion is a TRIM24:NTRK2 fusion. In other embodiments, the NTRK2 fusion is an AFAP1:NTRK2 fusion. In yet other embodiments, the NTRK2 fusion is a PAN3:NTRK2 fusion.

NTRK2 Gene Fusions and Fusion Proteins

NTRK2 gene fusions are generated by a fusion between at least a part of the NTRK gene and a part of another gene as a result of a translocation (including inversion) within a chromosome or between chromosomes. As a result of a translocation, the NTRK2 gene may be placed under the transcriptional control of the partner gene promoter, resulting in aberrant NTRK2 expression or activity, or overexpression of NTRK2. Alternatively or additionally, the partner gene can include a dimerization domain that causes NTRK2 to become constitutively activated. In some exemplary embodiments, the fusion partner is TRIM24 (Tripartite Motif Containing 24). In other exemplary embodiments, the fusion partner is AFAP1 (Actin Filament-Associated Protein 1). In yet other embodiments, the fusion partner is PAN3 (PABP-Dependent Poly(A) Nuclease 3).

As used herein, the 5'-region is upstream of, and the 3'-region is downstream of, a fusion junction or breakpoint in one of the component genes. NTRK2 and the gene or protein that it is fused to may be referred to as "fusion partners." Alternatively, they may be identified as an "NTRK2 gene fusion" or an "NTRK2 fusion protein," which are collectively termed "NTRK2 fusions." The NTRK2 fusions disclosed herein have a kinase activity. The phrase "having a kinase activity" as used in this application means having an activity as an enzyme phosphorylating the side chain of an amino acid, such as tyrosine. In some embodiments, the NTRK2 fusion may include an in-frame fusion of the coding sequences of NTRK2 and the fusion partner that introduces amino acids into the fusion protein that are not part of NTRK2 or the fusion partner.

Reference to "all or a portion" or "all or part" of an NTRK2 gene fusion or SEQ ID NO:1, SEQ ID NO:2, SEQ ID NO:5 or SEQ ID NO:7, means that the nucleotide sequence comprises the entire NTRK2 gene fusion nucleotide sequence or a fragment of that sequence that comprises the fusion junction breakpoint point between NTRK2 and its fusion partner (such as, e.g., TRIM24, AFAP1, or PAN3). The fragment may comprise 7, 8, 9, 10, 12, 14, 16, 18, 20, 21, 22, 23, 24, 25, 26, 27, 28, 29, 30, 35, 40, 45, 50, 60, 70, 80, 90, 100, 120, 150, 175, 200, 250, 300, or more nucleotides spanning the fusion junction of the NTRK2 gene fusion. Reference to "all or a portion" or "all or part" of a NTRK2 fusion protein or SEQ ID NO:3, SEQ ID NO:4, SEQ ID NO:6 or SEQ ID NO:8, means an amino acid sequence that comprises the entire NTRK2 fusion protein amino acid sequence or a fragment of that sequence that comprises the fusion junction breakpoint point between NTRK2 and its fusion partner (such as, e.g., TRIM24, AFAP1, or PAN3). The fragment may comprise 8, 10, 12, 14, 15, 16, 18, 20, 21, 22, 23, 24, 25, 26, 27, 28, 29, 30, 35, 40, 45, 50, 75, or more amino acids spanning the fusion junction.

In certain embodiments, a fusion includes an in-frame fusion of all or a portion of the gene TRIM24 (e.g., a TRIM24 promoter or a functional fragment thereof and one or more exons encoding TRIM24 or a fragment thereof) and an exon of the NTRK2 gene (e.g., one or more exons encoding an NTRK2 kinase domain or a functional fragment thereof). Such a fusion can be referred to as a TRIM24:NTRK2 fusion. In one embodiment, the TRIM24:NTRK2 fusion comprises sufficient TRIM24 and sufficient NTRK2 sequences to drive expression of a fusion protein that has kinase activity. In some embodiments, the TRIM24:NTRK2 fusion drives expression of a fusion protein that has elevated activity as compared with wild type NTRK2 in the same tissue or cell.

In a particular embodiment, the invention provides a TRIM24:NTRK2 gene fusion comprising the nucleotide sequence depicted in FIG. 1 (SEQ ID NO: 1), or a fragment thereof that includes the fusion junction. SEQ ID NO:1 comprises TRIM24 (NM_015905) up to exon number 12 (amino acid number 671) fused to NTRK2 (NM_006180), from exon number 16 (amino acid number 483). In some embodiments the TRIM24:NTRK2 gene fusion comprises a nucleotide sequence that is at least 85%, at least 90%, at least 95%, at least 97%, at least 98%, or at least 99% identical to all or part of SEQ ID NO:1. In another particular embodiment, the TRIM24:NTRK2 fusion has the nucleotide sequence depicted in FIG. 2 (SEQ ID NO:2), comprising TRIM24 (NM_015905) up to exon number 12 (amino acid number 671) fused to NTRK2 (NM_006180), from exon number 15 (amino acid number 467) or a fragment thereof that includes the fusion junction. In some embodiments, the TRIM24:NTRK2 gene fusion comprises a nucleotide sequence that is at least 85%, at least 90%, at least 95%, at least 97%, at least 98%, or at least 99% identical to all or part of SEQ ID NO:2.

In one embodiment, the TRIM24:NTRK2 gene fusion encodes a protein having all or part of the sequence depicted in FIG. 3 (SEQ ID NO:3) or a sequence that is at least 85%, at least 90%, at least 95%, at least 97%, at least 98%, or at least 99% identical to all or part of SEQ ID NO:3. In another embodiment, the TRIM24:NTRK2 fusion encodes a protein having all or part the sequence depicted in FIG. 4 (SEQ ID NO:4) or a sequence that is at least 85%, at least 90%, at least 95%, at least 97%, at least 98%, or at least 99% identical to all or part of SEQ ID NO:4.

In some embodiments, a fusion includes an in-frame fusion of all or a portion of gene AFAP1 (e.g., an AFAP1 promoter or a functional fragment thereof and one or more exons encoding AFAP1 or a fragment thereof) and an exon of gene NTRK2 (e.g., one or more exons encoding an NTRK2 kinase domain or a functional fragment thereof). Such a fusion can be referred to as an AFAP1:NTRK2 fusion. In one embodiment, the AFAP1:NTRK2 fusion comprises sufficient AFAP1 and sufficient NTRK2 sequences to drive expression of a fusion protein that has kinase activity. In some embodiments, the AFAP1:NTRK2 fusion drives expression of a fusion protein that has elevated activity as compared with wild type NTRK2 in the same tissue or cell.

In a particular embodiment, the AFAP1:NTRK2 fusion has the nucleotide sequence depicted in FIG. 5 (SEQ ID NO:5), comprising AFAP1 (NM_198595) up to exon number 13 (amino acid number 548) fused to NTRK2 (NM_006180), from exon number 12 (amino acid number 388) or a fragment thereof that includes the fusion junction. In some embodiments the AFAP1:NTRK2 gene fusion comprises a nucleotide sequence that is at least 85%, at least 90%, at least 95%, at least 97%, at least 98%, or at least 99% identical to all or part of SEQ ID NO:5. In one embodiment, the AFAP1:NTRK2 fusion encodes a protein having all or part of the sequence depicted in FIG. 6 (SEQ ID NO:6) or a sequence that is at least 85%, at least 90%, at least 95%, at least 97%, at least 98%, or at least 99% identical to all or part of SEQ ID NO:6.

In yet other embodiments, a fusion includes an in-frame fusion of all or a portion of gene PAN3 (e.g., a PAN3 promoter or a functional fragment thereof and one or more exons encoding PAN3 or a fragment thereof) and an exon of gene NTRK2 (e.g., one or more exons encoding an NTRK2 kinase domain or a functional fragment thereof). Such a fusion can be referred to as a PAN3:NTRK2 fusion. In one embodiment, the PAN3:NTRK2 fusion comprises sufficient PAN3 and sufficient NTRK2 sequences to drive expression of a fusion protein that has kinase activity. In some embodiments, the PAN3:NTRK2 fusion drives expression of a fusion protein that has elevated activity as compared with wild type NTRK2 in the same tissue or cell.

In a particular embodiment, the PAN3:NTRK2 fusion has the nucleotide sequence depicted in FIG. 7 (SEQ ID NO:7), comprising PAN3 (NM_175854) up to exon number 1 (amino acid number 143) fused to NTRK2 (NM_006180), from exon number 17 (amino acid number 546) or a fragment thereof that includes the fusion junction. In some embodiments the PAN3:NTRK2 gene fusion comprises a nucleotide sequence that is at least 85%, at least 90%, at least 95%, at least 97%, at least 98%, or at least 99% identical to all or part of SEQ ID NO:7. In one embodiment, the PAN3:NTRK2 fusion encodes a protein having all or part of the sequence depicted in FIG. 8 (SEQ ID NO:8) or a sequence that is at least 85%, at least 90%, at least 95%, at least 97%, at least 98%, or at least 99% identical to all or part of SEQ ID NO:8.

The nucleic acid sequences of NTRK2 gene fusions may be used as probes, primers, or bait to identify nucleotides from a biological sample that include, flank, or hybridize to NTRK2 fusions, such as TRIM24:NTRK2 (for example, all or part of SEQ ID NO:1 or SEQ ID NO:2), AFAP1:NTRK2 (for example, all or part of SEQ ID NO:5), or PAN3:NTRK2 (for example, all or part of SEQ ID NO:7), at, e.g., the fusion junctions. In certain embodiments, the probe, primer, or bait molecule is an oligonucleotide that allows capture, detection, and/or isolation of an NTRK2 gene fusion in a biological sample. In certain embodiments, the probes or primers derived from the nucleic acid sequences of NTRK2 gene fusions (e.g., from the fusion junctions) may be used, for example, for polymerase chain reaction (PCR) amplification. The oligonucleotide can comprise a nucleotide sequence substantially complementary to a fragment of the NTRK2 gene fusion nucleic acid molecules described herein. The sequence identity between the nucleic acid fragment, e.g., the oligonucleotide and the target NTRK2 gene fusion sequence, need not be exact, so long as the sequences are sufficiently complementary to allow the capture, detection, and/or isolation of the target sequence. In one embodiment, the nucleic acid fragment is a probe or primer that includes an oligonucleotide between about 5 and 25, e.g., between 10 and 20, or 10 and 15 nucleotides in length that includes the fusion junction of an NTRK2 fusion, such as, e.g., TRIM24:NTRK2 (for example, all or part of SEQ ID NO:1 or SEQ ID NO:2), AFAP1:NTRK2 (for example, all or part of SEQ ID NO:5), or PAN3:NTRK2 (for example, all or part of SEQ ID NO:7). In other embodiments, the nucleic acid fragment is a bait that includes an oligonucleotide between about 100 to 300 nucleotides, 130 and 230 nucleotides, or 150 and 200 nucleotides in length that includes the fusion junction of an NTRK2 fusion, such as, e.g., TRIM24:NTRK2 (for example, all or part of SEQ ID NO: or SEQ ID NO:2), AFAP1:NTRK2 (for example, all or part of SEQ ID NO:5), or PAN3:NTRK2 (for example, all or part of SEQ ID NO:7).

In certain embodiments, the nucleic acid fragments hybridize to a nucleotide sequence that includes a breakpoint or fusion junction, e.g., a breakpoint or fusion junction as identified by a slash ("/") in FIGS. 1, 2, 5, and 7. For example, the nucleic acid fragment can hybridize to a nucleotide sequence that includes the fusion junction between the TRIM24 transcript and the NTRK2 transcript (e.g, nucleotides 2014-2016 of SEQ ID NO:1, or nucleotides 2004-2006 of SEQ ID NO:2), or between the AFAP1 transcript and the NTRK2 transcript (e.g., nucleotides 1645-1647 of SEQ ID NO:5), or between the PAN3 transcript and the NTRK2 transcript (e.g., nucleotides 430-432 of SEQ ID NO:7), i.e., a nucleotide sequence that includes a portion of SEQ ID NO: 1, 2, 5, or 7. Examples include a nucleotide sequence within exons 1 to 12 of a TRIM24 gene and exons 15 or 16 to 22 of an NTRK2 gene (e.g., a portion of SEQ ID NO: comprising nucleotides 2010-2019, 2005-2024, 1990-2039, 1965-2064, 1940-2089, or 1915-2114; or a portion of SEQ ID NO:2 comprising nucleotides 2000-2009, 1995-2014, 1980-2029, 1955-2054, 1930-2079, or 1905-2104); a nucleotide sequence within exons 1 to 13 of an AFAP1 gene and exons 12 to 22 of an NTRK2 gene (e.g., a portion of SEQ ID NO:5 comprising nucleotides 1641-1650, 1636-1655, 1621-1670, 1596-1695, 1571-1720, or 1546-1745); and a nucleotide sequence within exon 1 of a PAN3 gene and exons 17-22 of an NTRK2 gene (e.g., the portion of SEQ ID NO:7 comprising nucleotides 426-435, 421-440, 406-455, 381-480, 354-504, or 330-529).

In other embodiments, the nucleic acid fragment includes a bait that comprises a nucleotide sequence that hybridizes to an NTRK2 gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait.

In exemplary embodiments, the nucleic acid fragments used as bait comprise a nucleotide sequence that includes a fusion junction between the TRIM24 transcript and the NTRK2 transcript, e.g, a nucleotide sequence within SEQ ID NO: 1 comprising nucleotides 2014-2016 (such as, e.g., a sequence comprising nucleotides 2010-2019, 2005-2024, 1990-2039, 1965-2064, 1940-2089, or 1915-2114 of SEQ ID NO: 1) or a nucleotide sequence within SEQ ID NO:2 comprising nucleotides 2004-2006 (such as, e.g., a sequence comprising nucleotides 2000-2009, 1995-2014, 1980-2029, 1955-2054, 1930-2079, or 1905-2104 of SEQ ID NO:2). In another exemplary embodiment, the nucleic acid sequences hybridize to a nucleotide sequence that includes a fusion junction between the AFAP1 transcript and the NTRK2 transcript, e.g., a nucleotide sequence within SEQ ID NO:5 comprising nucleotides 1645-1647 (such as, e.g., a sequence comprising nucleotides 1641-1650, 1636-1655, 1621-1670, 1596-1695, 1571-1720, or 1546-1745 of SEQ ID NO:5). In another exemplary embodiment, the nucleic acid sequences hybridize to a nucleotide sequence that includes a fusion junction between the PAN3 transcript and the NTRK2 transcript, e.g., a nucleotide sequence within SEQ ID NO:7 comprising nucleotides 430-432 (such as, e.g., a sequence comprising nucleotides 426-435, 421-440, 406-455, 381-480, 354-504, or 330-529 of SEQ ID NO:7).

Another aspect of the invention provides NTRK2 fusion proteins (such as, e.g., a purified or isolated TRIM24:NTRK2, AFAP1:NTRK2, or PAN3:NTRK2 fusion protein), biologically active or antigenic fragments thereof, and use of those polypeptides for detecting and/or modulating the biological activity (such as tumorigenic activity) of an NTRK2 fusion protein. Exemplary embodiments of the NTRK2 fusion proteins comprise the amino acid sequence set forth in SEQ ID NO:3, 4, 6, or 8, and fragments of those sequences.

In some embodiments, the NTRK2 fusion protein of the invention includes a fragment of a TRIM24 protein, an AFAP1 protein, or a PAN3 protein and a fragment of an NTRK2 protein. In one embodiment, the NTRK2 fusion protein is TRIM24:NTRK2 fusion protein having the amino acid sequence of SEQ ID NO:3 or a fragment thereof, such as, e.g., amino acids 670-674, 665-674, 662-681, or 652-691 of SEQ ID NO:3. In another embodiment, the NTRK2 fusion protein is a TRIM24:NTRK2 fusion protein having the amino acid sequence of SEQ ID NO:4 or a fragment thereof, such as, e.g., amino acids 670-674, 665-674, 662-681, or 652-691 of SEQ ID NO:4. In one embodiment, the NTRK2 fusion protein is an AFAP1:NTRK2 fusion protein having the amino acid sequence of SEQ ID NO:6 or a fragment thereof, such as, e.g., amino acids 547-551, 544-553, 539-558, or 529-568 of SEQ ID NO:6. In another embodiment, the NTRK2 fusion protein is a PAN3:NTRK2 fusion protein having the amino acid sequence of SEQ ID NO:8 or a fragment thereof, such as, e.g., amino acids 142-146, 138-147, 133-152, or 123-162 of SEQ ID NO:8.

In yet another embodiment, the NTRK2 fusion protein is a TRIM24:NTRK2 fusion protein comprising an amino acid sequence that is at least 85%, at least 90%, at least 95%, at least 97%, at least 98%, or at least 99% identical to SEQ ID NO:3 or a fragment thereof (e.g., amino acids 670-674, 665-674, 662-681, or 652-691 of SEQ ID NO:3). In another embodiment, the NTRK2 fusion protein is a TRIM24:NTRK2 fusion protein comprising an amino acid sequence that is at least 85%, at least 90%, at least 95%, at least 97%, at least 98%, or at least 99% identical to SEQ ID NO:4 or a fragment thereof (e.g., amino acids 670-674, 665-674, 662-681, or 652-691 of SEQ ID NO:4). In yet another embodiment, the NTRK2 fusion protein is an AFAP1: NTRK2 fusion protein comprising an amino acid sequence that is at least 85%, at least 90%, at least 95%, at least 97%, at least 98%, or at least 99% identical to all or part of SEQ ID NO:6 (e.g., amino acids 547-551, 544-553, 539-558, or 529-568 of SEQ ID NO:6). In another embodiment the NTRK2 fusion protein is a PAN3:NTRK2 fusion protein comprising an amino acid sequence that is at least 85%, at least 90%, at least 95%, at least 97%, at least 98%, or at least 99% identical to SEQ ID NO:8 or a fragment thereof (e.g., amino acids 142-146, 138-147, 133-152, or 123-162 of SEQ ID NO:8).

In certain embodiments, the NTRK2 fusion protein includes a functional kinase domain. In such embodiments, the NTRK2 fusion protein comprises elevated NTRK2 activity as compared with wild type NTRK2, for example, in a cancer cell, a non-cancer cell adjacent to the cancer cell, or a non-cancer cell from a control sample, such as a cancer free subject. In one exemplary embodiment, the NTRK2 fusion protein is a TRIM24:NTRK2 fusion and includes an NTRK2 tyrosine kinase domain or a functional fragment thereof. In another exemplary embodiment, the NTRK2 fusion protein is an AFAP1:NTRK2 fusion and includes an NTRK2 tyrosine kinase domain or a functional fragment thereof. In yet another embodiment, the NTRK2 fusion protein is a PAN3:NTRK2 fusion and includes an NTRK2 tyrosine kinase domain or a functional fragment thereof.

In another embodiment, the NTRK2 fusion protein or fragment is a peptide, e.g., an immunogenic peptide or protein, that contains a fusion junction with a heterologous protein as described herein. Such immunogenic peptides or proteins can be used for vaccine preparation for use in the treatment or prevention of cancers cause by or exacerbated by NTRK2 gene fusions and NTRK2 fusion proteins. In other embodiments, such immunogenic peptides or proteins can be used to raise antibodies specific to the fusion protein. In some embodiments, the NTRK2 fusion protein is present in combination with or is further conjugated to one or more adjuvant(s) or immunogen(s), e.g., a protein capable of enhancing an immune response to the NTRK2 fusion protein (e.g., a hapten, a toxoid, etc.). In some embodiments, the NTRK2 fusion protein is a TRIM24:NTRK2, AFAP1: NTRK2, or PAN3:NTRK2 fusion. In some embodiments, the NTRK2 fusion protein comprises the fusion junction of SEQ ID NO:3, 4, 6, or 8.

Thus, another aspect of the invention provides an antibody that binds to an NTRK2 fusion protein (such as, e.g., a TRIM24:NTRK2, an AFAP1:NTRK2, or a PAN3:NTRK2 fusion protein) or a fragment thereof. In certain embodiments, the antibody recognizes an NTRK2 fusion protein but does not recognize wild type NTRK2 or the wild type fusion partner (such as, e.g., TRIM24, AFAP1, or PAN3). In some embodiments, the antibody binds to an epitope comprising the fusion junction between NTRK2 and the fusion partner (e.g., the fusion junction of TRIM24:NTRK2, AFAP1:NTRK2, or PAN3:NTRK2). In one embodiment, the antibody binds to a TRIM24:NTRK2 fusion protein having the amino acid sequence of SEQ ID NO:3 or a fragment thereof, such as, e.g., amino acids 670-674, 665-674, 662-681, or 652-691 of SEQ ID NO:3. In one embodiment, the antibody binds to a TRIM24:NTRK2 fusion protein having the amino acid sequence of SEQ ID NO:4 or a fragment thereof, such as, e.g., amino acids 670-674, 665-674, 662-681, or 652-691 of SEQ ID NO:4. In other embodiments, the antibody binds to an AFAP1:NTRK2 fusion protein having the amino acid sequence of SEQ ID NO:6 or a fragment thereof, such as, e.g., amino acids 547-551, 544-553, 539-558, or 529-568 of SEQ ID NO:6. In yet other embodiments, the antibody binds to a PAN3:NTRK2 fusion protein having the amino acid sequence of SEQ ID NO:8 or a fragment thereof, such as, e.g., amino acids 142-146, 138-147, 133-152, or 123-162 of SEQ ID NO:8.

In certain embodiments, the antibodies of the invention inhibit and/or neutralize the biological activity of the NTRK2 fusion protein, and more specifically, in some embodiments, the kinase activity of the NTRK2 fusion protein. In other embodiments, the antibodies may be used to detect an NTRK2 fusion protein or to diagnose a patient suffering from a disease or disorder associated with the expression of an NTRK2 fusion protein.

Detection and Diagnostic Methods

In another aspect, the invention provides a method of determining the presence of an NTRK2 gene fusion or fusion protein, such as, e.g., a TRIM24:NTRK2, an AFAP1:NTRK2, or a PAN3:NTRK2 fusion as described herein. The presence of an NTRK2 gene fusion can indicate that the mammal providing the biological sample suffers from or is at risk of developing a disorder mediated by aberrant NTRK2 expression or activity, or overexpression of NTRK2, such as, e.g., a cancer. The presence of an NTRK2 gene fusion may also indicate that the cancer is treatable with an NTRK2 inhibitor (such as, e.g., an antibody specific to NTRK2) or an NTRK2 fusion inhibitor. In some embodiments the cancer is lung cancer. In some embodiments, the cancer is lung adenocarcinoma. In some embodiments the cancer is a glioma. In some embodiments, the cancer is a low grade glioma. In some embodiments, the cancer is squamous cell carcinoma. In some embodiments, the cancer is head and neck squamous cell carcinoma. In other embodiments, the cancer is a different cancer associated with aberrant expression or activity of NTRK2 or overexpression of NTRK2.

In one embodiment, the NTRK2 fusion detected is a nucleic acid molecule or a polypeptide. The method includes detecting whether an NTRK2 fusion nucleic acid molecule or polypeptide is present in a cell (e.g., a circulating cell or a cancer cell), a tissue (e.g., a tumor), or a sample (e.g., a tumor sample), from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample. The sample can be chosen from one or more of sample types: such as, e.g., tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

In some embodiments, the NTRK2 fusion is detected in a nucleic acid molecule by one or more methods chosen from nucleic acid hybridization assays (e.g. in situ hybridization, comparative genomic hybridization, microarray, Southern blot, northern blot), amplification-based assays (e.g., PCR, PCR-RFLP assay, or real-time PCR), sequencing and genotyping (e.g. sequence-specific primers, high-performance liquid chromatography, or mass-spectrometric genotyping), and screening analysis (including metaphase cytogenetic analysis by karyotype methods).

Hybridization Methods

In some embodiments, the reagent hybridizes to an NTRK2 gene fusion, such as, e.g., nucleotides 2014-2016, 2010-2019, 2005-2024, 1990-2039, 1965-2064, 1940-2089, or 1915-2114 of SEQ ID NO: 1. In alternate embodiments, the reagent detects the presence of nucleotides 2004-2006, 2000-2009, 1995-2014, 1980-2029, 1955-2054, 1930-2079, or 1905-2104 of SEQ ID NO:2, nucleotides 1645-1647, 1641-1650, 1636-1655, 1621-1670, 1596-1695, 1571-1720, or 1546-1745 of SEQ ID NO:5, or nucleotides 430-432, 426-435, 421-440, 406-455, 381-480, 354-504, or 330-529 of SEQ ID NO:7. In an alternate embodiment, the method includes the steps of obtaining a sample; exposing the sample to a nucleic acid probe which hybridizes to an mRNA or cDNA encoding an NTRK2 fusion protein that comprises amino acids 670-674, 665-674, 662-681, or 652-691 of SEQ ID NO:3, amino acids 670-674, 665-674, 662-681, or 652-691 of SEQ ID NO:4, amino acids 547-551, 544-553, 539-558, or 529-568 of SEQ ID NO:6, or amino acids 142-146, 138-147, 133-152, or 123-162 of SEQ ID NO:8, wherein hybridization of the probe to the mRNA or cDNA in the sample indicates the presence of an NTRK2 fusion polynucleotide.

Hybridization, as described throughout the specification, may be carried out under stringent conditions, e.g., medium or high stringency. See, e.g., J. Sambrook, E. F. Fritsch, and T. Maniatis, *Molecular Cloning: A Laboratory Manual*, Cold Spring Harbor Laboratory Pr; 2nd edition (1989); T. Brown, *Hybridization Analysis of DNA Blots. Current Protocols in Molecular Biology* at 21:2.10.1-2.10.16 (2001). High stringency conditions for hybridization refer to conditions under which two nucleic acids must possess a high degree of base pair homology to each other in order to hybridize. Examples of highly stringent conditions for hybridization include hybridization in 4×sodium chloride/sodium citrate (SSC), at 65 or 70° C., or hybridization in 4×SSC plus 50% formamide at about 42 or 50° C., followed by at least one, at least two, or at least three washes in 1×SSC, at 65 or 70° C. Another example of highly stringent conditions includes hybridization in 2×SSC; 10×Denhardt solution (Fikoll 400+PEG+BSA; ratio 1:1:1); 0.1% SDS; 5 mM EDTA; 50 mM $Na_2HPO_4$; 250 µg/ml of herring sperm DNA; 50 µg/ml of tRNA; or 0.25 M of sodium phosphate buffer, pH 7.2; 1 mM EDTA 7% SDS at 60° C.; followed by washing 2×SSC, 0.1% SDS at 60° C.

The nucleic acid fragments can be detectably labeled with, e.g., a radiolabel, a fluorescent label, a bioluminescent label, a chemiluminescent label, an enzyme label, a binding pair label (e.g., biotin/streptavidin), or can include an affinity tag or identifier (e.g., an adaptor, barcode or other sequence identifier). Labeled or unlabeled nucleic acids and/or nucleic acid fragments may be used in reagents for detecting, capturing, and/or isolating NTRK2 gene fusions, such as, e.g. TRIM24:NTRK2 (for example, all or part of SEQ ID NO: 1 or SEQ ID NO:2), AFAP1:NTRK2 (for example, all or part of SEQ ID NO:5), or PAN3:NTRK2 (for example, all or part of SEQ ID NO: 1 or SEQ ID NO:7).

In some embodiments, the method comprises performing chromosome in situ hybridization with chromosomal DNA from a biological sample to detect the presence of an NTRK2 gene fusion (such as, e.g., TRIM24:NTRK2, AFAP1:NTRK2, or PAN3:NTRK2, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of an NTRK2 gene fusion (such as, e.g., TRIM24:NTRK2, AFAP1:NTRK2, or PAN3:NTRK2, as disclosed herein). In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

Amplification-Based Assays

In certain embodiments, the method of detecting the presence of an NTRK2 gene fusion, comprises (a) performing a PCR amplification reaction with polynucleotides from a biological sample, wherein the amplification reaction utilizes a pair of primers which will amplify at least a fragment of the NTRK2 gene fusion, wherein the fragment comprises the fusion junction, wherein the first primer is in sense orientation and the second primer is in antisense orientation; and (b) detecting an amplification product, wherein the presence of the amplification product is indicative of the presence of an NTRK2 fusion polynucleotide in the sample. In specific exemplary embodiments, the NTRK2 gene fusion is TRIM24:NTRK2, such as, e.g., the gene fusion of SEQ ID NO: 1, or SEQ ID NO:2, or a fragment thereof, e.g., a nucleotide sequence comprising nucleotides 2014-2016, 2010-2019, 2005-2024, 1990-2039, 1965-2064, 1940-2089, or 1915-2114 of SEQ ID NO:1 or nucleotides 2004-2006, 2000-2009, 1995-2014, 1980-2029, 1955-2054, 1930-2079, or 1905-2104 of SEQ ID NO:2. In other exemplary embodiments, the gene fusion is AFAP1:NTRK2 such as, e.g. the gene fusion of SEQ ID NO:5 or a fragment thereof, e.g., a nucleotide sequence comprising nucleotides 1645-1647, 1641-1650, 1636-1655, 1621-1670, 1596-1695, 1571-1720, or 1546-1745 of SEQ ID NO:5. In some exemplary embodiments, the gene fusion is PAN3:NTRK2 such as, e.g. the gene fusion of SEQ ID NO:7 or a fragment thereof, e.g., a nucleotide sequence comprising nucleotides 430-432, 426-435, 421-440, 406-455, 381-480, 354-504, or 330-529 of SEQ ID NO:7. In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the NTRK2 gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 35, 40, 45, or 50 cycles). In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify a fragment of the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

Sequencing and Genotyping

Another method for determining the presence of an NTRK2 gene fusion molecule (such as, e.g., TRIM24:NTRK2, AFAP1:NTRK2, or PAN3:NTRK2, as disclosed herein) includes: sequencing a portion of the nucleic acid molecule (e.g., sequencing the portion of the nucleic acid molecule that comprises the fusion junction of an NTRK2 gene fusion), thereby determining that the NTRK2 gene fusion is present in the nucleic acid molecule. In some exemplary embodiments, the gene fusion is TRIM24:NTRK2. In other exemplary embodiments, the gene fusion is AFAP1:NTRK2. In yet other exemplary embodiments, the gene fusion is PAN3:NTRK2. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region of the template nucleic acid molecule, a DNA polymerase, a plurality of free nucleotides comprising adenine, thymine, cytosine, and guanine (dNTPs), and at least one chain terminating nucleotide (e.g., at least one di-deoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemiluminescent signal, such as light) in an amount that is proportional to the amount of ATP; (ii) annealing the primer to a single strand of the nucleic acid molecule; (iii) adding one of the four free nucleotides (dNTPs) to allow incorporation of the correct, complementary dNTP onto the template by the DNA polymerase and release of pyrophosphate stoichiometrically; (iv) converting the released pyrophosphate to ATP by the first enzyme; (v) generating a detectable signal by the second enzyme using the ATP; (vi) detecting the generated signal and analyzing the amount of signal generated in a program; (vii) removing the unincorporated nucleotides; and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of an NTRK2 fusion (such as, e.g., TRIM24:NTRK2, AFAP1:NTRK2, or PAN3:NTRK2, as disclosed herein) comprises analyzing a nucleic acid sample (e.g., DNA, cDNA, or RNA, or an amplification product thereof) by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of an NTRK2 fusion (such as, e.g., TRIM24:NTRK2, AFAP1:NTRK2, or PAN3:NTRK2, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Methods for Detecting Fusion Proteins

Another aspect of the invention provides a method of determining the presence of an NTRK2 fusion protein (such as, e.g., TRIM24:NTRK2, AFAP1:NTRK2, or PAN3:NTRK2, as disclosed herein) in a mammal. The method comprises the steps of obtaining a biological sample of a mammal (such as, e.g., from a human cancer), and exposing that sample to at least one reagent that detects an NTRK2 fusion protein (e.g., an antibody that recognizes the NTRK2 fusion but does not recognize the wild type NTRK2 or the wild type fusion partner) to determine whether an NTRK2 fusion protein is present in the biological sample. The detection of an NTRK2 fusion protein indicates the presence of a mutant NTRK2 in the mammal (such as, e.g., in the human cancer). In some embodiments, the NTRK2 fusion protein comprises an amino acid sequence having at least 85%, 90%, 95%, 97%, 98%, or 99% identity with an amino acid sequence of any one of SEQ ID NOs 3, 4, 6, and 8. In some embodiments the cancer is lung cancer, such as, e.g. lung adenocarcinoma. In some embodiments, the cancer is a glioma, such as, e.g. a low grade glioma. In some embodiments, the cancer is squamous cell carcinoma, such as, e.g., head and neck squamous cell carcinoma. In some embodiments, the reagent that detects an NTRK2 fusion protein can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag or identifier (e.g., an adaptor, barcode or other sequence identifier). In some embodiments, the labeled reagent can be detected using, e.g., autoradiography, microscopy (e.g., brightfield, fluorescence, or electron microscopy), ELISA, or immunohistochemistry. In some embodiments, the NTRK2 fusion protein is detected in a biological sample by a method chosen from one or more of: antibody-based detection (e.g., western blot, ELISA, immunohistochemistry), size-based detection methods (e.g., HPLC or mass spectrometry), or protein sequencing.

Antibody-Based Detection

In some embodiments, the method comprises performing a western blot with polypeptides from a biological sample to detect the presence of an NTRK2 fusion protein (such as, e.g., TRIM24:NTRK2, AFAP1:NTRK2, or PAN3:NTRK2, as disclosed herein). In some embodiments, the western blot comprises the steps of: separating the polypeptides by gel electrophoresis; transferring the polypeptides from the gel to a membrane (e.g., a nitrocellulose or polyvinylidene difluoride (PVDF) membrane); blocking the membrane to prevent nonspecific binding by incubating the membrane in a dilute solution of protein (e.g., 3-5% bovine serum albumin (BSA) or non-fat dry milk in Tris-Buffered Saline (TBS) or I-Block, with a minute percentage (e.g., 0.1%) of detergent, such as, e.g., Tween 20 or Triton X-100); exposing the polypeptides to at least one reagent that detects an NTRK2 fusion protein (e.g., an antibody that recognizes the NTRK2 fusion but does not recognize the wild type NTRK2 or the wild type fusion partner); removing unbound or non-specifically bound reagent by washing; and detecting the binding of the reagent with the target protein. In some embodiments, the method comprises two-step detection: exposing the polypeptides to a primary antibody that specifically binds to an NTRK2 fusion protein; removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the reagent that detects an NTRK2 fusion protein (e.g., the fusion specific antibody, or the secondary antibody) is directly labeled for detection. In other embodiments, the reagent is linked to an enzyme, and the method further comprises adding a substrate of the enzyme to the membrane; and developing the membrane by detecting a detectable signal produced by the reaction between the enzyme and the substrate. For example, the reagent may be linked with horseradish peroxidase to cleave a chemiluminescent agent as a substrate, producing luminescence in proportion to the amount of the target protein for detection.

In some embodiments, the method comprises performing ELISA with polypeptides from a biological sample to detect the presence of an NTRK2 fusion protein (such as, e.g., TRIM24:NTRK2, AFAP1:NTRK2, or PAN3:NTRK2, as disclosed herein). In some embodiments, the ELISA is chosen from, e.g., direct ELISA, indirect ELISA, sandwich ELISA, and competitive ELISA.

In one embodiment, the direct ELISA comprises the steps of: attaching polypeptides from a biological sample to a surface; blocking the surface to prevent nonspecific binding by incubating the surface in a dilute solution of protein; exposing the polypeptides to an antibody that specifically binds to an NTRK2 fusion protein (e.g., an antibody that recognizes the NTRK2 fusion (such as, e.g., TRIM24:NTRK2, AFAP1:NTRK2, or PAN3:NTRK2, as disclosed herein) but does not recognize the wild type NTRK2 or the wild type fusion partner); removing unbound or non-specifically bound antibody by washing; and detecting the binding of the antibody with the target protein. In some embodiments, the antibody is directly labeled for detection. In other embodiments, the antibody is linked to an enzyme, and the method further comprises adding a substrate of the enzyme; and detecting a detectable signal produced by the reaction between the enzyme and the substrate.

In another embodiment, the indirect ELISA comprises the steps of: attaching polypeptides from a biological sample to a surface; blocking the surface to prevent nonspecific binding by incubating the surface in a dilute solution of protein; exposing the polypeptides to a primary antibody that specifically binds to an NTRK2 fusion protein (such as, e.g., TRIM24:NTRK2, AFAP1:NTRK2, or PAN3:NTRK2, as disclosed herein); removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the secondary antibody is directly labeled for detection. In other embodiments, the secondary antibody is linked to an enzyme, and the method further comprises adding a substrate of the enzyme; and detecting a detectable signal produced by the reaction between the enzyme and the substrate.

In some embodiments, the method comprises performing immunohistochemistry with polypeptides from a biological sample to detect the presence of an NTRK2 fusion protein (such as, e.g., TRIM24:NTRK2, AFAP1:NTRK2, or PAN3:NTRK2, as disclosed herein). In some embodiments, the immunohistochemistry comprises the steps of: fixing a cell or a tissue section (e.g., by paraformaldehyde or formalin treatment); permeabilizing the cell or tissue section to allow target accessibility; blocking the cell or tissue section to prevent nonspecific binding; exposing the cell or tissue section to at least one reagent that detects an NTRK2 fusion protein (e.g., an antibody that recognizes the NTRK2 fusion but does not recognize the wild type NTRK2 or the wild type fusion partner); removing unbound or non-specifically bound reagent by washing; and detecting the binding of the reagent with the target protein. In some embodiments, the reagent is directly labeled for detection. In other embodiments, the reagent is linked to an enzyme, and the method further comprises adding a substrate of the enzyme; and detecting a detectable signal produced by the reaction between the enzyme and the substrate. In some embodiments, the immunohistochemistry may comprise the two-step detection as in the indirect ELISA.

Size-Based Detection Methods

In some embodiments, the method of determining the presence of an NTRK2 fusion (such as, e.g., TRIM24:NTRK2, AFAP1:NTRK2, or PAN3:NTRK2, as disclosed herein) comprises analyzing a protein sample by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of an NTRK2 fusion (such as, e.g., TRIM24:NTRK2, AFAP1:NTRK2, or PAN3:NTRK2, as disclosed herein) comprises analyzing a protein sample by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of an NTRK2 gene fusion or an NTRK2 fusion protein in a patient can lead to assignment of the patient to the newly identified patient population that bears the NTRK2 fusion. Because this patient population can suffer from or be susceptible to a disorder associated with aberrant NTRK2 expression or activity, or overexpression of NTRK2, detection of the NTRK2 fusion can also lead to diagnosis of such disorder. Thus, a further aspect of the invention provides a method of stratifying a patient population (e.g., assigning a patient, to a group or class) and/or diagnosing a patient, comprising: obtaining a biological sample from the patient, contacting the sample with at least one reagent that detects an NTRK2 gene fusion or an NTRK2 fusion protein to determine whether an NTRK2 fusion is present in the biological sample. The detection of an NTRK2 fusion indicates that the patient belongs to the newly identified patient population that bears the NTRK2 fusion, and/or the presence of a disorder associated with aberrant NTRK2 expression or activity, or overexpression of NTRK2, such as, e.g., certain cancers. The detection of a NTRK2 fusion also identifies a new subtype of cancer, which is characterized by the presence of the NTRK2 fusion, such as e.g., lung cancer (e.g., lung adenocarcinoma), glioma (e.g., low grade glioma), or squamous cell carcinoma (e.g., head and neck squamous cell carcinoma). In certain embodiments, the NTRK2 fusion is TRIM24:NTRK2. In some embodiments, the TRIM24:NTRK2 fusion has all or part of the nucleotide and/or amino acid sequence (such as, e.g., the fusion junction) set forth in SEQ ID NO: 1 and SEQ ID NO:3, respectively. In some embodiments, the TRIM24:NTRK2 fusion has all or part of the nucleotide and/or amino acid sequence (such as, e.g., the fusion junction) set forth in SEQ ID NO:2 and SEQ ID NO:4, respectively. In other embodiments, the NTRK2 fusion is AFAP1:NTRK2. In some embodiments, the AFAP1:NTRK2 fusion has all or part of the nucleotide and/or amino acid sequence (such as, e.g., the fusion junction) set forth in SEQ ID NO:5 and SEQ ID NO:6, respectively. In yet other embodiments, the NTRK2 fusion is PAN3:NTRK2. In some embodiments, the PAN3:NTRK2 fusion has all or part of the nucleotide and/or amino acid sequence (such as, e.g., the fusion junction) set forth in SEQ ID NO:7 and SEQ ID NO:8, respectively.

In some embodiments, the NTRK2 gene fusion or NTRK2 fusion protein is detected prior to initiating, during, and/or after, a treatment of a patient with, e.g., an NTRK2 inhibitor (such as, e.g., a kinase inhibitor) or an NTRK2 fusion inhibitor. In one embodiment, the NTRK2 gene fusion or NTRK2 fusion protein is detected at the time the patient is diagnosed with a cancer. In other embodiment, the NTRK2 fusion is detected at a pre-determined interval, e.g., a first point in time and at least at a subsequent point in time. In certain embodiments, in response to detection of an NTRK2 fusion, such as, e.g., TRIM24:NTRK2, AFAP1:NTRK2, or PAN3:NTRK2, the method further includes one or more of:

(1) stratifying a patient population (e.g., assigning a patient, to a group or class);

(2) identifying or selecting the patient as likely or unlikely to respond to a treatment, e.g., a NTRK2 inhibitor treatment (e.g., a kinase inhibitor treatment), or a NTRK2 fusion inhibitor treatment as described herein;

(3) selecting a treatment regimen, e.g., administering or not administering a preselected therapeutic agent, such as, e.g., an NTRK2 inhibitor (e.g., a pan NTRK-1,2,3 inhibitor, or an NTRK2 specific inhibitor) or an NTRK2 fusion inhibitor;

(4) prognosticating the time course of the disease in the patient (e.g., evaluating the likelihood of increased or decreased patient survival); or (5) monitoring the effectiveness of treatment (e.g., by detecting a reduction in the level of NTRK2 gene fusion or fusion protein in a patient sample).

In certain embodiments, upon detection of an NTRK2 gene fusion or NTRK2 fusion protein in a patient's biological sample, the patient is identified as likely to respond to a treatment that comprises an NTRK2 inhibitor (e.g., a pan NTRK-1,2,3 inhibitor, or an NTRK2 specific inhibitor) or an NTRK2 fusion inhibitor. In some embodiments, the NTRK2 fusion detected is a TRIM24:NTRK2 fusion. In alternate embodiments, the NTRK2 fusion detected is an AFAP1:NTRK2 fusion. In some embodiments, the NTRK2 fusion detected is a PAN3:NTRK2 fusion.

A further aspect of the invention provides a method of selecting a treatment option by detecting an NTRK2 fusion. The method comprises obtaining a biological sample from a patient and exposing the sample to at least one reagent that detects an NTRK2 gene fusion or fusion protein to determine whether an NTRK2 fusion is present in the biological sample. The detection of the NTRK2 gene fusion or fusion protein indicates the likelihood of the patient responding to treatment with an NTRK inhibitor or an NTRK2 fusion inhibitor. The method may be augmented or personalized by evaluating the effect of a variety of NTRK2 inhibitors or NTRK2 fusion inhibitors on the biological sample shown to contain an NTRK2 gene fusion or fusion protein to determine the most appropriate inhibitor to administer. In certain embodiments, the NTRK2 fusion is TRIM24:NTRK2. In some embodiments, the TRIM24:NTRK2 fusion has all or part of the nucleotide and/or amino acid sequence (such as, e.g., the fusion junction) set forth in SEQ ID NO: 1 and SEQ ID NO:3, respectively. In some embodiments, the TRIM24:NTRK2 fusion has all or part of the nucleotide and/or amino acid sequence (such as, e.g., the fusion junction) set forth in SEQ ID NO:2 and SEQ ID NO:4, respectively. In other embodiments, the NTRK2 fusion is AFAP1:NTRK2. In some embodiments, the AFAP1:NTRK2 fusion has all or part of the nucleotide and/or amino acid sequence (such as, e.g., the fusion junction) set forth in SEQ ID NO:5 and SEQ ID NO:6, respectively. In yet other embodiments, the NTRK2 fusion is PAN3:NTRK2. In some embodiments, the PAN3:NTRK2 fusion has all or part of the nucleotide and/or amino acid sequence (such as, e.g., the fusion junction) set forth in SEQ ID NO:7 and SEQ ID NO:8, respectively.

Methods of Treatment

Alternatively, or in combination with the detection and diagnostic methods described herein, the invention provides method for treating the newly identified patient population and the new NTRK2 fusion cancer subtype, which are characterized by the presence of an NTRK2 fusion. The patient population and cancer subtype can be associated with or predict the onset of a condition mediated by aberrant NTRK2 expression or activity, or overexpression of NTRK2, such as, e.g., a cancer or a tumor harboring an NTRK2 fusion. In certain embodiments, the cancer or tumor harboring an NTRK2 fusion is lung cancer (e.g., lung adenocarcinoma), glioma (e.g., low grade glioma), or squamous cell carcinoma (e.g., head and neck squamous cell carcinoma). The methods comprise administering a therapeutic agent, e.g., an NTRK2 inhibitor (such as, e.g., a pan-NTRK-1,2,3 inhibitor, or an NTRK2-specific inhibitor) or an NTRK2 fusion inhibitor, i.e., an inhibitor that blocks the activity of the NTRK2 fusion but not wild type NTRK2 (such as, e.g., an antibody specific to a TRIM24:NTRK2, AFAP1:NTRK2, or PAN3:NTRK2 fusion protein, or any one of the antibodies described above; or an RNA inhibitor that recognizes NTRK2 or the fusion junction of an NTRK2 gene fusion, including but not limited to siRNA, dsRNA, shRNA, or any other antisense nucleic acid inhibitor), alone or in combination with e.g., other chemotherapeutic agents or procedures, in an amount sufficient to treat a condition mediated by aberrant NTRK2 expression or activity, or overexpression of NTRK2, by one or more of the following: e.g., impeding growth of a cancer, causing a cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression—free survival, prolonging time to progression, and/or enhancing quality of life.

In certain embodiments, the NTRK2 fusion proteins of the invention may be inhibited by a NTRK2 inhibitor or a NTRK2 fusion inhibitor. In some embodiments, the therapeutic agent is a NTRK2 inhibitor, such as, e.g., a compound, biological or chemical, which inhibits, directly or indirectly, the expression and/or activity of NTRK2. For example, the NTRK2 inhibitors may be an antibody (such as, e.g., antibodies specific to NTRK2) or a small molecule inhibitor. In some embodiments, the inhibitors may act directly on NTRK2 itself, modify the activity of NTRK2, or inhibit the expression of NTRK2. In other embodiments, the inhibitors may indirectly inhibit NTRK2 activity by inhibiting the activity of proteins or molecules other than NTRK2 itself. For example, the inhibitors may modulate the activity of regulatory kinases that phosphorylate or dephosphorylate NTRK2, interfere with binding of ligands, or inhibit the activity of interacting or downstream proteins or molecules.

Exemplary small molecule inhibitors include pan-kinase inhibitors with activity against several different kinases (including NTRK2) or specific inhibitors (e.g., inhibitors specific to NTRKs, or specific to NTRK2). Exemplary pan-kinase inhibitors include, but are not limited to those listed in International Patent Publications WO 2006/123113, WO2011/133637, WO 2012/116217, WO 2012/034091, and WO 2012/034095, WO 2013/074518, and WO 2013/174876. Exemplary NTRK-specific inhibitors include those described in WO 2011/006074. Each of these applications is incorporated herein in its entirety for its disclosure of such inhibitors.

In some embodiments, the NTRK2 fusion protein is inhibited by an NTRK2 fusion inhibitor, such as, e.g., an antibody that recognizes all or part of an NTRK2 fusion (such as, e.g., a TRIM24:NTRK2 fusion protein, an AFAP1:NTRK2 fusion protein, or a PAN3:NTRK2 fusion protein) but does not recognize wild type NTRK2 or wild type fusion partner (such as, e.g., TRIM24, AFAP1, or PAN3). In some embodiments, the NTRK2 fusion protein (such as, e.g., a TRIM24:NTRK2 fusion protein, an AFAP1:NTRK2 fusion protein, or a PAN3:NTRK2 fusion protein) is inhibited by an agent that inhibits transcription or translation of the fusion protein, e.g., an RNA inhibitor that recognizes the NTRK2 coding sequence, the binding partner (e.g., TRIM24, AFAP1, or PAN3), or the binding partner: NTRK2 fusion junction, including but not limited to small interfering RNA (siRNA), double stranded RNA (dsRNA), short-hairpin RNA (shRNA), or any other antisense nucleic acid inhibitor. In some embodiments, the NTRK2 fusion inhibited is selected from all or a portion of any one of SEQ ID NOs: 1-8.

As used herein, and unless otherwise specified, a "therapeutically effective amount" of a compound is an amount sufficient to provide a therapeutic benefit in the treatment or management of a condition mediated by aberrant NTRK2 expression or activity, or overexpression of NTRK2, such as, delaying or minimizing one or more symptoms associated with a cancer or a tumor harboring an NTRK2 fusion (such as, e.g., TRIM24:NTRK2, AFAP1:NTRK2, or PAN3:NTRK2, as disclosed herein). A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the condition mediated by aberrant NTRK2 expression or activity or overexpression of NTRK2, or enhances the therapeutic efficacy of another therapeutic agent.

In certain embodiments, the cancer or tumor harboring an NTRK2 fusion is lung cancer, such as, e.g., lung adenocarcinoma. In other embodiments, the cancer or tumor harboring an NTRK2 fusion is glioma, such as, e.g., a low grade glioma. In some embodiments, the cancer or tumor harboring an NTRK2 fusion is squamous cell carcinoma, such as, e.g., head and neck squamous cell carcinoma.

In some embodiments, the patient to be treated is suffering from lung cancer, such as, e.g., lung adenocarcinoma, and the method for treating the condition comprises administering to the patient a therapeutically effective amount of an NTRK2 inhibitor or an NTRK2 fusion inhibitor. In some embodiments, the patient to be treated is suffering from glioma, such as, e.g., a lower grade glioma, and the method for treating the condition comprises administering to the patient a therapeutically effective amount of an NTRK2 inhibitor or an NTRK2 fusion inhibitor. In some embodiments, the patient to be treated is suffering from squamous cell carcinoma, such as, e.g., head and neck squamous cell carcinoma, and the method for treating the condition comprises administering to the patient a therapeutically effective amount of an NTRK2 inhibitor or an NTRK2 fusion inhibitor.

Screening Methods

Therapeutic agents, such as e.g., NTRK2 inhibitors or NTRK2 fusion inhibitors, used in the therapeutic methods of the invention can be evaluated using the screening assays described herein. Thus, the invention provides a method of identifying an agent useful for treating a condition mediated by aberrant NTRK2 expression or activity, or overexpression of NTRK2, such as, e.g., a cancer or a tumor harboring an NTRK2 fusion, such as e.g., lung cancer (e.g., lung adenocarcinoma), glioma (e.g., low grade glioma), or squamous cell carcinoma (e.g., head and neck squamous cell carcinoma), comprising contacting a cell expressing an NTRK2 gene fusion or NTRK2 fusion protein with a candidate agent and determining whether the expression level of the fusion is decreased or a biological function associated with the fusion is altered. In one embodiment, therapeutic agents can be evaluated in a cell-free system, e.g., a cell lysate or in a reconstituted system. In other embodiments, the therapeutic agents are evaluated in a cell in culture, e.g., a cell expressing an NTRK2 fusion (e.g., a mammalian cell, a tumor cell or cell line, a recombinant cell). In yet other embodiments, the therapeutic agents are evaluated in vivo (e.g., an NTRK2 fusion-expressing cell present in a subject, e.g., an animal subject (e.g., an in vivo animal model)).

Exemplary parameters to evaluate in determining the efficacy of a therapeutic agent for treating a condition mediated by aberrant NTRK2 expression or activity, or overexpression of NTRK2, such as, e.g., a cancer or a tumor harboring an NTRK2 fusion include one or more of:

(i) a change in binding activity, e.g., direct binding of the candidate agent to an NTRK fusion protein; or a binding competition between a known ligand and the candidate agent to an NTRK2 fusion protein;

(ii) a change in kinase activity, e.g., phosphorylation levels of an NTRK fusion protein (e.g., an increased or decreased phosphorylation or autophosphorylation); or a change in phosphorylation of a target of an NTRK2 kinase—in certain embodiments, a change in kinase activity, e.g., phosphorylation, is detected by any of western blot (e.g., using an anti-NTRK2 antibody or a phosphor-specific antibody, detecting a shift in the molecular weight of an NTRK2 fusion protein), mass spectrometry, immunoprecipitation, immunohistochemistry, immunomagnetic beads, among others;

(iii) a change in an activity of a cell containing an NTRK fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor; or (v) a change in the level, e.g., expression (transcription and/or translation) level of an NTRK2 fusion protein or nucleic acid molecule; or (vi) a change in an activity of a signaling pathway involving NTRK2, e.g., phosphorylation or activity of an interacting or downstream target, or expression level of a target gene.

In some embodiments, the NTRK fusion is a TRIM24:NTRK2 fusion, an AFAP1:NTRK2 fusion, or a PAN3:NTRK2 fusion.

In one embodiment, a change in the activity of an NTRK2 fusion, or interaction of an NTRK2 fusion with a downstream ligand detected in a cell free assay in the presence of a candidate agent indicates that the candidate agent will be effective as a therapeutic agent for treatment of a condition mediated by aberrant NTRK2 expression or activity, or overexpression of NTRK2, such as, e.g., a cancer or a tumor harboring an NTRK2 fusion (such as, e.g., lung cancer (e.g., lung adenocarcinoma), glioma (e.g., low grade glioma), or squamous cell carcinoma (e.g., head and neck squamous cell carcinoma)).

In other embodiments, a change in an activity of a cell expressing an NTRK2 fusion, such as, e.g., TRIM24:NTRK2, AFAP1:NTRK2, or PAN3:NTRK2, as disclosed herein (e.g., a mammalian cell, a tumor cell or cell line, a recombinant cell) is detected in a cell in culture. In one embodiment, the cell is a recombinant cell that is modified to express an NTRK2 fusion nucleic acid, e.g., is a recombinant cell transfected with an NTRK2 fusion nucleic acid. The transfected cell can show a change in response to the expressed NTRK2 fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, or transformed morphology, in the presence of the candidate agent can be indicative of an inhibitor of an NTRK2 fusion. In other embodiments, a change in binding activity or phosphorylation of NTRK2 or its interacting or downstream proteins or molecules as described herein is detected.

In yet other embodiment, a change in a tumor present in an animal subject (e.g., an in vivo animal model) is detected. In one embodiment, a tumor containing animal or a xenograft comprising cells expressing an NTRK fusion (e.g., tumorigenic cells expressing an NTRK fusion) is employed. The therapeutic agents can be administered to the animal subject and a change in the tumor is evaluated. In one embodiment, the change in the tumor includes one or more of a tumor growth, tumor size, tumor burden, or survival, is evaluated. A decrease in one or more of tumor growth, tumor size, tumor burden, or an increased survival is indicative that the candidate agent is an inhibitor or modulator.

In another aspect of the invention provides a method or assay for screening for agents that modulate (e.g., inhibit) the expression or activity of an NTRK2 fusion as described herein. The method includes contacting e.g., an NTRK2 fusion, or a cell expressing an NTRK2 fusion, with a candidate agent; and detecting a change in a parameter associated with an NTRK2 fusion, e.g., a change in the expression or an activity of the NTRK2 fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the NTRK2 fusion is detected, the candidate agent is identified as an inhibitor. In another embodiment, if an increase in expression or activity of the NTRK2 fusion is detected, the candidate agent is identified as an activator. In certain embodiments, the NTRK fusion is an NTRK2 gene fusion or NTRK2 fusion protein, where in the fusion is e.g., a TRIM24:NTRK2 fusion, an AFAP1:NTRK2 fusion, or a PAN3:NTRK2 fusion.

In one embodiment, the contacting step is detected in a cell-free system, e.g., a cell lysate or in a reconstituted system. In other embodiments, the contacting step is detected in a cell in culture, e.g., a cell expressing an NTRK2 fusion (e.g., a mammalian cell, a tumor cell or cell line, a recombinant cell). In yet other embodiments, the contacting step is detected in vivo (e.g., an NTRK2 expressing cell present in a subject, e.g., an animal subject (e.g., an in vivo animal model)).

Exemplary parameters evaluated in identifying an agent that modulates the activity of an NTRK fusion, e.g., an NTRK2 fusion (e.g., a TRIM24:NTRK2 fusion, an AFAP1:NTRK2 fusion, or a PAN3:NTRK2 fusion) include one or more of:

(i) a change in binding activity, e.g., direct binding of the candidate agent to an NTRK2 fusion protein; a binding competition between a known ligand and the candidate agent to an NTRK fusion protein;

(ii) a change in kinase activity, e.g., phosphorylation levels of an NTRK2 fusion protein (e.g., an increased or decreased phosphorylation or autophosphorylation); or a change in phosphorylation of a target of an NTRK kinase—in certain embodiments, a change in kinase activity, e.g., phosphorylation, is detected by any of western blot (e.g., using an anti-NTRK2 antibody or a phosphor-specific antibody, detecting a shift in the molecular weight of an NTRK2 fusion protein), mass spectrometry, immunoprecipitation, immunohistochemistry, immunomagnetic beads, among others;

(iii) a change in an activity of a cell containing an NTRK fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor;

(v) a change in the level, e.g., expression (transcription and/or translation) level of an NTRK2 fusion protein or nucleic acid molecule; or (vi) a change in an activity of a signaling pathway involving NTRK2, e.g., phosphorylation or activity of an interacting or downstream target, or expression level of a target gene.

Methods for Validating NTRK Fusions

NTRK gene fusions (such as, e.g., TRIM24:NTRK2 gene fusions, AFAP1:NTRK2 gene fusions, or PAN3:NTRK2 gene fusions) may be evaluated to ensure that the breakpoints are in-frame and can produce a protein product containing the full kinase domain, i.e., that the breakpoint occurs such that complete triplet codons are intact, and that the RNA sequence will produce a viable protein. The NTRK gene fusion can be transfected into cells to confirm that the protein is functionally active with respect to kinase activity and oncogenic activity. cDNA encoding the NTRK fusion protein can be produced by standard solid-phase DNA synthesis. Alternatively the NTRK fusion cDNA can be produced by RT-PCR using tumor mRNA extracted from samples containing the gene fusion. The DNA subcloned can be cloned into an appropriate vector and characterized by DNA sequence analysis or in vitro/in vivo expression analyses.

Expression vectors containing the NTRK gene fusion (such as, e.g., a TRIM24:NTRK2 gene fusion, an AFAP1:NTRK2 gene fusion, or a PAN3:NTRK2 gene fusion) can be introduced into host cells to thereby produce an NTRK2 fusion protein (such as, e.g., a TRIM24:NTRK2 fusion protein, an AFAP1:NTRK2 fusion protein, or a PAN3:NTRK2 fusion protein). The NTRK2 fusion protein expression vector can be a yeast expression vector, a vector for expression in insect cells, e.g., a baculovirus expression vector, or a vector suitable for expression in mammalian cells. Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell.

Cells harboring the expression vector carrying the recombinant NTRK gene fusion can then be tested for production of the unique fusion protein via standard western blotting using either an antibody probe that detects the gene product itself or that recognizes a tag peptide (e.g., FLAG tag) that can be added to the gene product via the expression vector (using standard, commercially available reagents). Western blotting can be used to confirm the ectopic expression of the encoded NTRK2 fusion protein by comparing the samples from cells transfected with the vector containing the NTRK2 gene fusion cDNA to cells transfected with the empty expression vector. The functional activity can be assessed by measuring the level of phosphorylation on the kinase or substrate. Comparison of the level of phosphorylation activity between the wild type (normal) form of NTRK2 and the NTRK2 fusion protein can indicate if the NTRK2 fusion protein has elevated activity that could drive oncogenic activity. Whether the NTRK gene fusion is oncogenic can be assessed by measuring capacity of the expressed NTRK2 fusion protein to transform cells, that is, to enable cells to grow and proliferate under conditions which are not permissive for growth of normal cells. One commonly used method of measuring the transforming activity of a kinase is by assessing if expression of the gene product can allow BaF3 cells to grow in the absence of the growth factor IL3, which is required for the survival and growth of BaF3 cells. Another assay for measuring transforming activity is a soft agar growth assay. This is another standard method which tests the capacity of an introduced gene product to confer the ability to grow in a soft agar matrix, or anchorage-independent conditions. These methods and others can be used to test the oncogenic activity of an NTRK2 gene fusion (such as, e.g., a TRIM24:NTRK2 gene fusion, an AFAP1:NTRK2 gene fusion, a PAN3:NTRK2 gene fusion) and provide a level of validation of an NTRK2 fusion protein (such as, e.g., a TRIM24:NTRK2 fusion protein, an AFAP1:NTRK2 fusion protein, or a PAN3:NTRK2 fusion protein) as a potential target for treating patients that harbor these fusions.

A change in an activity of a cell can be detected in a cell in culture, e.g., a cell expressing a fusion (e.g., a mammalian cell, a tumor cell or cell line, a recombinant cell). The transfected cell can show a change in response to the expressed fusion, e.g., increased proliferation, changes in morphology, increased tumorigenicity, and/or an acquired transformed phenotype.

To further validate the biological implication of the gene fusion, a change in any of the activities of the cell, e.g., the recombinant cell, in the presence of a known inhibitor of one of the fusion partners, e.g., an NTRK2 inhibitor, can be detected. For example, a decrease in one or more of: proliferation, tumorigenicity, or transformed morphology, in the presence of the NTRK2 inhibitor can be indicative of an inhibitor of a fusion. In other embodiments, a change in binding activity or phosphorylation of NTRK2 or its interacting or downstream proteins or molecules as described herein is detected.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of "or" means "and/or" unless stated otherwise. The use of the term "including," as well as other forms, such as "includes" and "included," is not limiting. All ranges given in the application encompass the endpoints unless stated otherwise.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for detecting the presence of a TRIM24:NTRK2 gene fusion in a patient in need thereof, said method comprising:
   (a) contacting a biological sample from the patient with an oligonucleotide that hybridizes to the fusion junction of the TRIM24:NTRK2 gene fusion, and detecting binding between the TRIM24:NTRK2 gene fusion and the oligonucleotide; or
   (b) sequencing or amplifying a portion of a nucleic acid from the patient, and detecting the presence of a nucleotide sequence comprising at least the TRIM24:NTRK2,
   wherein the TRIM24:NTRK2 gene fusion to be detected comprises SEQ ID NO:1 or 2 or a portion thereof, wherein the portion comprises the fusion junction.

2. The method of claim 1, wherein the oligonucleotide hybridizes under stringent conditions to
   (a) a fragment of SEQ ID NO:1 comprising at least nucleotides 2010-2019 of SEQ ID NO:1; or
   (b) a fragment of SEQ ID NO:2 comprising at least nucleotides 2000-2009 of SEQ ID NO:2.

3. The method of claim 1, wherein the patient is suffering from or susceptible to a cancer.

4. The method of claim 3, wherein the cancer is lung adenocarcinoma, low grade glioma, squamous cell carcinoma, or head and neck squamous cell carcinoma.

5. The method of claim 4, wherein the cancer is lung adenocarcinoma.

6. The method of claim 4, wherein the cancer is low grade glioma.

7. The method of claim 4, wherein the cancer is squamous cell carcinoma.

8. The method of claim 4, wherein the cancer is head or neck squamous cell carcinoma.

* * * * *

```
                        SEQUENCE LISTING

<160> NUMBER OF SEQ ID NOS: 8

<210> SEQ ID NO 1
<211> LENGTH: 3087
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
atggaggtgg cggtggagaa ggcggtggcg gcggcggcag cggcctcggc tgcggcctcc      60 gggggccct  cggcggcgcc gagcggggag aacgaggcca agagtcggca gggcccggac     120
tcggagcgcg gcggcgaggc ggcccggctc aacctgttgg acacttgcgc cgtgtgccac     180
cagaacatcc agagccgggc gcccaagctg ctgccctgcc tgcactcttt ctgccagcgc     240
tgcctgcccg cgccccagcg ctacctcatg ctgcccgcgc ccatgctggg ctcggccgag     300
accccgccac ccgtccctgc ccccggctcg ccggtcagcg gctcgtcgcc gttcgccacc     360
caagttggag tcattcgttg cccagtttgc agccaagaat gtgcagagag acacatcata     420
gataactttt ttgtgaagga cactactgag gttcccagca gtacagtaga aaagtcaaat     480
caggtatgta caagctgtga ggacaacgca gaagccaatg ggttttgtgt agagtgtgtt     540
gaatggctct gcaagacgtg tatcagagct catcagaggg taaagttcac aaaagaccac     600
actgtcagac agaaagagga agtatctcca gaggcagttg gtgtcaccag ccagcgacca     660
gtgttttgtc cttttcataa aaaggagcag ctgaagctgt actgtgagac atgtgacaaa     720
ctgacatgtc gagactgtca gttgttagaa cataaagagc atagatacca atttatagaa     780
gaagcttttc agaatcagaa agtgatcata gatacactaa tcaccaaact gatggaaaaa     840
acaaaataca taaaattcac aggaaatcag atccaaaaca gaattattga agtaaatcaa     900
aatcaaaagc aggtggaaca ggatattaaa gttgctatat ttacactgat ggtagaaata     960
aataaaaaag gaaaagctct actgcatcag ttagagagcc ttgcaaagga ccatcgcatg    1020
aaacttatgc aacaacaaca ggaagtggct ggactctcta acaattgga gcatgtcatg    1080 cattttctct aatgggcagt ttccagtggc agcagtacag cattacttta tagcaaacga    1140
ctgattacat accggttacg gcacctcctt cgtgcaaggt gtgatgcatc cccagtgacc    1200
aacaacacca tccaatttca ctgtgatcct agtttctggg ctcaaaatat catcaactta    1260
ggttctttag taatcgagga taaagagagc cagccacaaa tgcctaagca gaatcctgtc    1320
gtggaacaga ttcacagcc accaagtggt ttatcatcaa accagttatc caagttccca    1380
acacagatca gcctagctca attacggctc cagcatatgc agcaacaggt aatggctcag    1440
aggcaacagg tgcaacggag gccagcacct gtgggtttac caaaccctag aatgcagggg    1500
cccatccagc aaccttccat ctctcatcag caaccgcctc cacgtttgat aaactttcag    1560
aatcacagcc ccaaacccaa tggaccagtt cttcctcctc atcctcaaca actgagatat    1620
ccaccaaacc agaacatacc acgacaagca ataaagccaa accccctaca gatggctttc    1680
ttggctcaac aagccataaa acagtggcag atcagcagtg acagggaac cccatcaact    1740 accaacagca catcctctac tccttccagc cccacgatta ctagtgcagc aggatatgat    1800
```

```
ggaaaggctt ttggttcacc tatgatcgat ttgagctcac cagtgggagg gtcttataat    1860
cttccctctc ttccggatat tgactgttca agtactatta tgctggacaa tattgtgagg    1920
aaagatacta atatagatca tggccagcca agaccaccct caaacagaac ggtccagtca    1980
ccaaattcat cagtgccatc tccaggcctt gcaggcccag cctccgttat cagcaatgat    2040
gatgactctg ccagcccact ccatcacatc tccaatggga gtaacactcc atcttcttcg    2100
gaaggtggcc cagatgctgt cattattgga atgaccaaga tccctgtcat tgaaaatccc    2160
cagtactttg gcatcaccaa cagtcagctc aagccagaca catttgttca gcacatcaag    2220
cgacataaca ttgttctgaa aagggagcta ggcgaaggag cctttggaaa agtgttccta    2280
gctgaatgct ataacctctg tcctgagcag gacaagatct tggtggcagt gaagaccctg    2340
aaggatgcca gtgacaatgc acgcaaggac ttccaccgtg aggccgagct cctgaccaac    2400
ctccagcatg agcacatcgt caagttctat ggcgtctgcg tggagggcga ccccctcatc    2460
atggtctttg agtacatgaa gcatgggggac ctcaacaagt tcctcagggc acacggccct    2520
gatgccgtgc tgatggctga gggcaacccg cccacggaac tgacgcagtc gcagatgctg    2580
catatagccc agcagatcgc cgcgggcatg gtctacctgg cgtcccagca cttcgtgcac    2640
cgcgatttgg ccaccaggaa ctgcctggtc ggggagaact tgctggtgaa aatcggggac    2700
tttgggatgt cccgggacgt gtacagcact gactactaca gggtcggtgg ccacacaatg    2760
ctgcccattc gctggatgcc tccagagagc atcatgtaca ggaaattcac gacggaaagc    2820
gacgtctgga gcctgggggt cgtgttgtgg gagattttca cctatggcaa acagccctgg    2880
taccagctgt caaacaatga ggtgatagag tgtatcactc agggccgagt cctgcagcga    2940
ccccgcacgt gccccagga ggtgtatgag ctgatgctgg ggtgctggca gcgagagccc    3000
cacatgagga gaacatcaa gggcatccat accctccttc agaacttggc caaggcatct    3060
ccggtctacc tggacattct aggctag                                       3087
```

<210> SEQ ID NO 2
<211> LENGTH: 3125
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 2

```
atggaggtgg cggtggagaa ggcggtggcg gcggcggcag cggcctcggc tgcggcctcc      60
ggggggccct cggcggcgcc aacgaggccg agagtcggca gggcccggac tcggagcgcg     120
gcggcgaggc ggcccggctc aacctgttgg acacttgcgc cgtgtgccac cagaacatcc     180
agagccgggc gcccaagctg ctgccctgcc tgcactcttt ctgccagcgc tgcctgcccg     240
cgccccagcg ctacctcatg ctgccccgcgc ccatgctggg ctcggccgag accccgccac     300
ccgtccctgc ccccggctcg ccggtcagcg gctcgtcgcc gttcgccacc caagttggag     360
tcattcgttg cccagtttgc agccaagaat gtgcagagag acacatcata gataactttt     420
ttgtgaagga cactactgag gttcccagca gtacagtaga aaagtcaaat caggtatgta     480
caagctgtga ggacaacgca gaagccaatg ggttttgtgt agagtgtgtt gaatggctct     540
gcaagacgtg tatcagagct catcagaggg taaagttcac aaaagaccac actgtcgagac     600 agaaagagga agtatctcca gaggcagttg gtgtcaccag ccagcgacca gtgttttgtc     660
```

```
cttttcataa aaaggagcag ctgaagctgt actgtgagac atgtgacaaa ctgacatgtc      720
gagactgtca gttgttagaa cataaagagc atagatacca atttatagaa gaagcttttc      780
agaatcagaa agtgatcata gatacactaa tcaccaaact gatggaaaaa acaaaataca      840
taaaattcac aggaaatcag atccaaaaca gaattattga agtaaatcaa atcaaaagc       900 aggtggaaca ggatattaaa gttgctatat ttacactgat ggtagaaata aataaaaaag      960
gaaaagctct actgcatcag ttagagagcc ttgcaaagga ccatcgcatg aaacttatgc     1020
aacaacaaca ggaagtggct ggactctcta acaattgga gcatgtcatg cattttcta      1080 aatgggcagt ttccagtggc agcagtacag cattacttta tagcaaacga ctgattacat     1140
accggttacg gcacctcctt cgtgcaaggt gtgatgcatc cccagtgacc aacaacacca     1200
tccaatttca ctgtgatcct agtttctggg ctcaaaatat catcaactta ggttctttag     1260
taatcgagga taaagagagc cagccacaaa tgcctaagca gaatcctgtc gtggaacaga     1320
attcacagcc accaagtggt ttatcatcaa accagttatc caagttccca acacagatca     1380
gcctagctca attacggctc cagcatatgc agcaacaggt aatggctcag aggcaacagg     1440
tgcaacggag ccagcacct gtgggtttac caaaccctag aatgcagggg cccatccagc     1500
aaccttccat ctctcatcag caaccgcctc cacgtttgat aaactttcag aatcacagcc     1560
ccaaacccaa tggaccagtt cttcctcctc atcctcaaca actgagatat ccaccaaacc     1620
agaacatacc acgacaagca ataaagccaa acccctaca gatggctttc ttggctcaac     1680
aagccataaa acagtggcag atcagcagtg acagggaaac cccatcaact accaacagca     1740
catcctctac tccttccagc cccacgatta ctagtgcagc aggatatgat ggaaaggctt     1800
ttggttcacc tatgatcgat ttgagctcac cagtgggagg gtcttataat cttccctctc     1860
ttccggatat tgactgttca agtactatta tgctggacaa tattgtgagg aaagatacta     1920
atatagatca tggccagcca agaccaccct caaacagaac ggtccagtca ccaaattcat     1980
cagtgccatc tccaggcctt gcagatttct catggtttgg atttgggaaa gtaaaatcaa     2040
gacaaggtgt tggcccagcc tccgttatca gcaatgatga tgactctgcc agcccactcc     2100
atcacatctc caatgggagt aacactccat cttcttcgga aggtggccca gatgctgtca     2160
ttattggaat gaccaagatc cctgtcattg aaaatcccca gtactttggc atcaccaaca     2220
gtcagctcaa gccagacaca tttgttcagc acatcaagcg acataacatt gttctgaaaa     2280
gggagctagg cgaaggagcc tttggaaaag tgttcctagc tgaatgctat aacctctgtc     2340
ctgagcagga caagatcttg gtggcagtga agacccctgaa ggatgccagt gacaatgcac     2400
gcaaggactt ccaccgtgag gccgagctcc tgaccaacct ccagcatgag cacatcgtca     2460
agttctatgg cgtctgcgtg gagggcgacc ccctcatcat ggtctttgag tacatgaagc     2520
atgggaccct caacaagttc ctcagggcac acggccctga tgccgtgctg atggctgagg     2580
gcaacccgcc cacggaactg acgcagtcgc agatgctgca tatagcccag cagatcgccg     2640
cgggcatggt ctacctggcg tcccagcact tcgtgcaccg cgatttggcc accaggaact     2700
gcctggtcgg ggagaacttg ctggtgaaaa tcggggactt tgggatgtcc cgggacgtgt     2760
acagcactga ctactacagg gtcggtggcc acacaatgct gcccattcgc tggatgcctc     2820
cagagagcat catgtacagg aaattcacga cggaaagcga cgtctggagc ctggggtcg      2880 tgttgtggga gattttcacc tatggcaaac agccctggta ccagctgtca aacaatgagg     2940
tgatagagtg tatcactcag ggccgagtcc tgcagcgacc ccgcacgtgc ccccaggagg     3000
tgtatgagct gatgctgggg tgctggcagc gagagcccca catgaggaag aacatcaagg     3060
```

```
gcatccatac cctccttcag aacttggcca aggcatctcc ggtctacctg gacattctag    3120
gctag                                                                3125
```

<210> SEQ ID NO 3
<211> LENGTH: 1028
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

```
Met Glu Val Ala Val Glu Lys Ala Val Ala Ala Ala Ala Ala Ala Ser
1               5                   10                  15

Ala Ala Ala Ser Gly Gly Pro Ser Ala Ala Pro Ser Gly Glu Asn Glu
            20                  25                  30

Ala Glu Ser Arg Gln Gly Pro Asp Ser Glu Arg Gly Gly Glu Ala Ala
        35                  40                  45

Arg Leu Asn Leu Leu Asp Thr Cys Ala Val Cys His Gln Asn Ile Gln
50                  55                  60

Ser Arg Ala Pro Lys Leu Leu Pro Cys Leu His Ser Phe Cys Gln Arg
65                  70                  75                  80

Cys Leu Pro Ala Pro Gln Arg Tyr Leu Met Leu Pro Ala Pro Met Leu
                85                  90                  95

Gly Ser Ala Glu Thr Pro Pro Val Pro Ala Pro Gly Ser Pro Val
            100                 105                 110

Ser Gly Ser Ser Pro Phe Ala Thr Gln Val Gly Val Ile Arg Cys Pro
        115                 120                 125

Val Cys Ser Gln Glu Cys Ala Glu Arg His Ile Ile Asp Asn Phe Phe
130                 135                 140

Val Lys Asp Thr Thr Glu Val Pro Ser Ser Thr Val Glu Lys Ser Asn
145                 150                 155                 160

Gln Val Cys Thr Ser Cys Glu Asp Asn Ala Glu Ala Asn Gly Phe Cys
                165                 170                 175

Val Glu Cys Val Glu Trp Leu Cys Lys Thr Cys Ile Arg Ala His Gln
            180                 185                 190

Arg Val Lys Phe Thr Lys Asp His Thr Val Arg Gln Lys Glu Glu Val
        195                 200                 205

Ser Pro Glu Ala Val Gly Val Thr Ser Gln Arg Pro Val Phe Cys Pro
210                 215                 220

Phe His Lys Lys Glu Gln Leu Lys Leu Tyr Cys Glu Thr Cys Asp Lys
225                 230                 235                 240

Leu Thr Cys Arg Asp Cys Gln Leu Leu Glu His Lys Glu His Arg Tyr
                245                 250                 255

Gln Phe Ile Glu Glu Ala Phe Gln Asn Gln Lys Val Ile Ile Asp Thr
            260                 265                 270

Leu Ile Thr Lys Leu Met Glu Lys Thr Lys Tyr Ile Lys Phe Thr Gly
        275                 280                 285

Asn Gln Ile Gln Asn Arg Ile Ile Glu Val Asn Gln Asn Gln Lys Gln
290                 295                 300

Val Glu Gln Asp Ile Lys Val Ala Ile Phe Thr Leu Met Val Glu Ile
305                 310                 315                 320

Asn Lys Lys Gly Lys Ala Leu Leu His Gln Leu Glu Ser Leu Ala Lys
                325                 330                 335
```

```
Asp His Arg Met Lys Leu Met Gln Gln Gln Glu Val Ala Gly Leu
                340                 345                 350

Ser Lys Gln Leu Glu His Val Met His Phe Ser Lys Trp Ala Val Ser
        355                 360                 365

Ser Gly Ser Ser Thr Ala Leu Leu Tyr Ser Lys Arg Leu Ile Thr Tyr
    370                 375                 380

Arg Leu Arg His Leu Leu Arg Ala Arg Cys Asp Ala Ser Pro Val Thr
385                 390                 395                 400

Asn Asn Thr Ile Gln Phe His Cys Asp Pro Ser Phe Trp Ala Gln Asn
                405                 410                 415

Ile Ile Asn Leu Gly Ser Leu Val Ile Glu Asp Lys Glu Ser Gln Pro
            420                 425                 430

Gln Met Pro Lys Gln Asn Pro Val Val Glu Gln Asn Ser Gln Pro Pro
        435                 440                 445

Ser Gly Leu Ser Ser Asn Gln Leu Ser Lys Phe Pro Thr Gln Ile Ser
    450                 455                 460

Leu Ala Gln Leu Arg Leu Gln His Met Gln Gln Val Met Ala Gln
465                 470                 475                 480

Arg Gln Gln Val Gln Arg Arg Pro Ala Pro Val Gly Leu Pro Asn Pro
                485                 490                 495

Arg Met Gln Gly Pro Ile Gln Gln Pro Ser Ile Ser His Gln Gln Pro
            500                 505                 510

Pro Pro Arg Leu Ile Asn Phe Gln Asn His Ser Pro Lys Pro Asn Gly
        515                 520                 525

Pro Val Leu Pro Pro His Pro Gln Gln Leu Arg Tyr Pro Pro Asn Gln
    530                 535                 540

Asn Ile Pro Arg Gln Ala Ile Lys Pro Asn Pro Leu Gln Met Ala Phe
545                 550                 555                 560

Leu Ala Gln Gln Ala Ile Lys Gln Trp Gln Ile Ser Ser Gly Gln Gly
                565                 570                 575

Thr Pro Ser Thr Thr Asn Ser Thr Ser Thr Pro Ser Ser Pro Thr
            580                 585                 590

Ile Thr Ser Ala Ala Gly Tyr Asp Gly Lys Ala Phe Gly Ser Pro Met
        595                 600                 605

Ile Asp Leu Ser Ser Pro Val Gly Gly Ser Tyr Asn Leu Pro Ser Leu
    610                 615                 620

Pro Asp Ile Asp Cys Ser Ser Thr Ile Met Leu Asp Asn Ile Val Arg
625                 630                 635                 640

Lys Asp Thr Asn Ile Asp His Gly Gln Pro Arg Pro Ser Asn Arg
                645                 650                 655

Thr Val Gln Ser Pro Asn Ser Ser Val Pro Ser Pro Gly Leu Ala Gly
            660                 665                 670

Pro Ala Ser Val Ile Ser Asn Asp Asp Ser Ala Ser Pro Leu His
        675                 680                 685

His Ile Ser Asn Gly Ser Asn Thr Pro Ser Ser Ser Glu Gly Gly Pro
    690                 695                 700

Asp Ala Val Ile Ile Gly Met Thr Lys Ile Pro Val Ile Glu Asn Pro
705                 710                 715                 720

Gln Tyr Phe Gly Ile Thr Asn Ser Gln Leu Lys Pro Asp Thr Phe Val
                725                 730                 735

Gln His Ile Lys Arg His Asn Ile Val Leu Lys Arg Glu Leu Gly Glu
            740                 745                 750
```

```
Gly Ala Phe Gly Lys Val Phe Leu Ala Glu Cys Tyr Asn Leu Cys Pro
            755                 760                 765

Glu Gln Asp Lys Ile Leu Val Ala Val Lys Thr Leu Lys Asp Ala Ser
    770                 775                 780

Asp Asn Ala Arg Lys Asp Phe His Arg Glu Ala Glu Leu Leu Thr Asn
785                 790                 795                 800

Leu Gln His Glu His Ile Val Lys Phe Tyr Gly Val Cys Val Glu Gly
                805                 810                 815

Asp Pro Leu Ile Met Val Phe Glu Tyr Met Lys His Gly Asp Leu Asn
            820                 825                 830

Lys Phe Leu Arg Ala His Gly Pro Asp Ala Val Leu Met Ala Glu Gly
        835                 840                 845

Asn Pro Pro Thr Glu Leu Thr Gln Ser Gln Met Leu His Ile Ala Gln
    850                 855                 860

Gln Ile Ala Ala Gly Met Val Tyr Leu Ala Ser Gln His Phe Val His
865                 870                 875                 880

Arg Asp Leu Ala Thr Arg Asn Cys Leu Val Gly Glu Asn Leu Leu Val
                885                 890                 895

Lys Ile Gly Asp Phe Gly Met Ser Arg Asp Val Tyr Ser Thr Asp Tyr
            900                 905                 910

Tyr Arg Val Gly Gly His Thr Met Leu Pro Ile Arg Trp Met Pro Pro
        915                 920                 925

Glu Ser Ile Met Tyr Arg Lys Phe Thr Thr Glu Ser Asp Val Trp Ser
    930                 935                 940

Leu Gly Val Val Leu Trp Glu Ile Phe Thr Tyr Gly Lys Gln Pro Trp
945                 950                 955                 960

Tyr Gln Leu Ser Asn Asn Glu Val Ile Glu Cys Ile Thr Gln Gly Arg
                965                 970                 975

Val Leu Gln Arg Pro Arg Thr Cys Pro Gln Glu Val Tyr Glu Leu Met
            980                 985                 990

Leu Gly Cys Trp Gln Arg Glu Pro  His Met Arg Lys Asn  Ile Lys Gly
        995                 1000                1005

Ile His  Thr Leu Leu Gln Asn  Leu Ala Lys Ala Ser  Pro Val Tyr
    1010                1015                1020

Leu Asp  Ile Leu Gly
    1025

<210> SEQ ID NO 4
<211> LENGTH: 1044
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Glu Val Ala Val Glu Lys Ala Val Ala Ala Ala Ala Ala Ala Ser
1               5                   10                  15

Ala Ala Ala Ser Gly Gly Pro Ser Ala Ala Pro Ser Gly Glu Asn Glu
            20                  25                  30

Ala Glu Ser Arg Gln Gly Pro Asp Ser Glu Arg Gly Gly Glu Ala Ala
        35                  40                  45

Arg Leu Asn Leu Leu Asp Thr Cys Ala Val Cys His Gln Asn Ile Gln
    50                  55                  60

Ser Arg Ala Pro Lys Leu Leu Pro Cys Leu His Ser Phe Cys Gln Arg
```

-continued

```
            65                  70                  75                  80
Cys Leu Pro Ala Pro Gln Arg Tyr Leu Met Leu Pro Ala Pro Met Leu
                    85                  90                  95
Gly Ser Ala Glu Thr Pro Pro Val Pro Ala Pro Gly Ser Pro Val
                100                 105                 110
Ser Gly Ser Ser Pro Phe Ala Thr Gln Val Gly Val Ile Arg Cys Pro
                115                 120                 125
Val Cys Ser Gln Glu Cys Ala Glu Arg His Ile Ile Asp Asn Phe Phe
            130                 135                 140
Val Lys Asp Thr Thr Glu Val Pro Ser Thr Val Glu Lys Ser Asn
145                 150                 155                 160
Gln Val Cys Thr Ser Cys Glu Asp Asn Ala Glu Ala Asn Gly Phe Cys
                165                 170                 175
Val Glu Cys Val Glu Trp Leu Cys Lys Thr Cys Ile Arg Ala His Gln
                180                 185                 190
Arg Val Lys Phe Thr Lys Asp His Thr Val Arg Gln Lys Glu Glu Val
            195                 200                 205
Ser Pro Glu Ala Val Gly Val Thr Ser Gln Arg Pro Val Phe Cys Pro
    210                 215                 220
Phe His Lys Lys Glu Gln Leu Lys Leu Tyr Cys Glu Thr Cys Asp Lys
225                 230                 235                 240
Leu Thr Cys Arg Asp Cys Gln Leu Leu Glu His Lys Glu His Arg Tyr
                245                 250                 255
Gln Phe Ile Glu Glu Ala Phe Gln Asn Gln Lys Val Ile Ile Asp Thr
            260                 265                 270
Leu Ile Thr Lys Leu Met Glu Lys Thr Lys Tyr Ile Lys Phe Thr Gly
        275                 280                 285
Asn Gln Ile Gln Asn Arg Ile Ile Glu Val Asn Gln Asn Gln Lys Gln
    290                 295                 300
Val Glu Gln Asp Ile Lys Val Ala Ile Phe Thr Leu Met Val Glu Ile
305                 310                 315                 320
Asn Lys Lys Gly Lys Ala Leu Leu His Gln Leu Glu Ser Leu Ala Lys
                325                 330                 335
Asp His Arg Met Lys Leu Met Gln Gln Gln Glu Val Ala Gly Leu
                340                 345                 350
Ser Lys Gln Leu Glu His Val Met His Phe Ser Lys Trp Ala Val Ser
            355                 360                 365
Ser Gly Ser Ser Thr Ala Leu Leu Tyr Ser Lys Arg Leu Ile Thr Tyr
    370                 375                 380
Arg Leu Arg His Leu Leu Arg Ala Arg Cys Asp Ala Ser Pro Val Thr
385                 390                 395                 400
Asn Asn Thr Ile Gln Phe His Cys Asp Pro Ser Phe Trp Ala Gln Asn
                405                 410                 415
Ile Ile Asn Leu Gly Ser Leu Val Ile Glu Asp Lys Glu Ser Gln Pro
            420                 425                 430
Gln Met Pro Lys Gln Asn Pro Val Val Glu Gln Asn Ser Gln Pro Pro
        435                 440                 445
Ser Gly Leu Ser Ser Asn Gln Leu Ser Lys Phe Pro Thr Gln Ile Ser
    450                 455                 460
Leu Ala Gln Leu Arg Leu Gln His Met Gln Gln Val Met Ala Gln
465                 470                 475                 480
Arg Gln Gln Val Gln Arg Arg Pro Ala Pro Val Gly Leu Pro Asn Pro
                485                 490                 495
```

```
Arg Met Gln Gly Pro Ile Gln Pro Ser Ile Ser His Gln Gln Pro
            500                 505                 510

Pro Pro Arg Leu Ile Asn Phe Gln Asn His Ser Pro Lys Pro Asn Gly
        515                 520                 525

Pro Val Leu Pro Pro His Pro Gln Gln Leu Arg Tyr Pro Pro Asn Gln
    530                 535                 540

Asn Ile Pro Arg Gln Ala Ile Lys Pro Asn Pro Leu Gln Met Ala Phe
545                 550                 555                 560

Leu Ala Gln Gln Ala Ile Lys Gln Trp Gln Ile Ser Ser Gly Gln Gly
                565                 570                 575

Thr Pro Ser Thr Thr Asn Ser Thr Ser Ser Thr Pro Ser Ser Pro Thr
            580                 585                 590

Ile Thr Ser Ala Ala Gly Tyr Asp Gly Lys Ala Phe Gly Ser Pro Met
        595                 600                 605

Ile Asp Leu Ser Ser Pro Val Gly Gly Ser Tyr Asn Leu Pro Ser Leu
    610                 615                 620

Pro Asp Ile Asp Cys Ser Ser Thr Ile Met Leu Asp Asn Ile Val Arg
625                 630                 635                 640

Lys Asp Thr Asn Ile Asp His Gly Gln Pro Arg Pro Pro Ser Asn Arg
                645                 650                 655

Thr Val Gln Ser Pro Asn Ser Ser Val Pro Ser Pro Gly Leu Ala Asp
            660                 665                 670

Phe Ser Trp Phe Gly Phe Gly Lys Val Lys Ser Arg Gln Gly Val Gly
        675                 680                 685

Pro Ala Ser Val Ile Ser Asn Asp Asp Ser Ala Ser Pro Leu His
    690                 695                 700

His Ile Ser Asn Gly Ser Asn Thr Pro Ser Ser Ser Glu Gly Gly Pro
705                 710                 715                 720

Asp Ala Val Ile Ile Gly Met Thr Lys Ile Pro Val Ile Glu Asn Pro
                725                 730                 735

Gln Tyr Phe Gly Ile Thr Asn Ser Gln Leu Lys Pro Asp Thr Phe Val
            740                 745                 750

Gln His Ile Lys Arg His Asn Ile Val Leu Lys Arg Glu Leu Gly Glu
        755                 760                 765

Gly Ala Phe Gly Lys Val Phe Leu Ala Glu Cys Tyr Asn Leu Cys Pro
    770                 775                 780

Glu Gln Asp Lys Ile Leu Val Ala Val Lys Thr Leu Lys Asp Ala Ser
785                 790                 795                 800

Asp Asn Ala Arg Lys Asp Phe His Arg Glu Ala Glu Leu Leu Thr Asn
                805                 810                 815

Leu Gln His Glu His Ile Val Lys Phe Tyr Gly Val Cys Val Glu Gly
            820                 825                 830

Asp Pro Leu Ile Met Val Phe Glu Tyr Met Lys His Gly Asp Leu Asn
        835                 840                 845

Lys Phe Leu Arg Ala His Gly Pro Asp Ala Val Leu Met Ala Glu Gly
    850                 855                 860

Asn Pro Pro Thr Glu Leu Thr Gln Ser Gln Met Leu His Ile Ala Gln
865                 870                 875                 880

Gln Ile Ala Ala Gly Met Val Tyr Leu Ala Ser Gln His Phe Val His
                885                 890                 895

Arg Asp Leu Ala Thr Arg Asn Cys Leu Val Gly Glu Asn Leu Leu Val
            900                 905                 910
```

Lys Ile Gly Asp Phe Gly Met Ser Arg Asp Val Tyr Ser Thr Asp Tyr
        915                 920                 925

Tyr Arg Val Gly Gly His Thr Met Leu Pro Ile Arg Trp Met Pro Pro
        930                 935                 940

Glu Ser Ile Met Tyr Arg Lys Phe Thr Thr Glu Ser Asp Val Trp Ser
945                 950                 955                 960

Leu Gly Val Val Leu Trp Glu Ile Phe Thr Tyr Gly Lys Gln Pro Trp
                965                 970                 975

Tyr Gln Leu Ser Asn Asn Glu Val Ile Glu Cys Ile Thr Gln Gly Arg
            980                 985                 990

Val Leu Gln Arg Pro Arg Thr Cys Pro Gln Glu Val Tyr Glu Leu Met
        995                 1000                1005

Leu Gly Cys Trp Gln Arg Glu Pro His Met Arg Lys Asn Ile Lys
        1010                1015                1020

Gly Ile His Thr Leu Leu Gln Asn Leu Ala Lys Ala Ser Pro Val
        1025                1030                1035

Tyr Leu Asp Ile Leu Gly
        1040

<210> SEQ ID NO 5
<211> LENGTH: 3003
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

```
atggaagagt taatagttga acttcgtctc tttcttgaac tcctggacca tgaatatcta      60
acctcaactg tcagggagaa aaaggcagtg ataaccaaca ttctgctaag aatacagtca     120
tccaaaggtt ttgatgtgaa ggaccatgct cagaagcagg agaccgctaa cagcctgcca     180
gcccctcctc agatgcccct gccggagatc cctcagccct ggctgcctcc tgacagtggg     240
cctccaccat tgccaacatc ctccctccca gaaggttatt atgaggaagc tgtgccgctg     300
agccccggaa aagctccgga atacatcaca tcaaattatg attccgatgc gatgagcagc     360
tcttatgagt cgtatgatga agaggaggag gatgggaagg gaagaaaaac ccggcaccag     420
tggccctccg aggaggcctc catggacctg gtcaaggacg ccaaaatctg cgccttcctg     480
ctgcggaaga gcggttcgg ccagtggacc aagttgctct gcgtcatcaa agacaccaaa     540
ctgctgtgct ataaaagttc caaggaccag cagcctcaga tggaactgcc actccaaggc     600
tgtaacatta cgtacatccc gaaagacagc aaaagaaga agcacgagct gaagattact     660
cagcagggca cggacccgct tgttctcgcc gtccagagca aggaacaggc cgagcagtgg     720
ctgaaggtga tcaaagaagc ctacagtggt tgtagtggcc ccgtggattc agagtgtcct     780
cctccaccaa gctccccggt gcacaaggca gaactggaga gaaactgtc ttcagagaga     840 cccagctcag atggggaggg tgttgtggaa atggaatta ccacatgtaa tggaaaggag     900
caagtgaaga ggaagaaaag ttccaaatca gaggccaagg gcactgtgtc gaaagtcact     960
gggaaaaaaa tcaccaagat catcagtctg ggaaagaaaa agccgtccac agacgagcag    1020
acctcctcag ctgaggaaga tgttcccacc tgcggctatc tgaacgtgct ctccaacagc    1080
cgctggcgag agcgctggtg ccgagtgaaa gataacaagc tcattttcca caggacagg    1140 accgacctga gaccatat tgtgtctatt ccgctccgtg gctgcgaggt gatcccgggt    1200
```

```
ttggattcta acatcctct gacgttccgg ctgctgcgca acggccagga ggttgcagta      1260
ttggaggcat cttcttctga agacatgggc aggtggattg ggatttact cgcagagacg      1320 ggatcgtcca cagacccgga ggctctgcac tatgactaca ttgatgtgga gatgtctgca     1380
agtgtcattc agacagccaa acagaccttc tgtttcatga acaggcgtgt tatatctgct    1440
aacccatatc tagggggcac ctccaacggc tatgcccacc ccagcgggac ggcacttcat    1500
tatgacgatg tcccgtgcat caacggctcg ctcaagggta aaagccccc cgtggcgtct     1560 aatggggtca caggaaaagg gaagactctg agcagtcagc caaagaaagc ggatcccgcg    1620
gctgttgtga aaggacggg ttcgagtgca acccaaatt atcctgatgt aatttatgaa      1680
gattatggaa ctgcagcgaa tgacatcggg gacaccacga acagaagtaa tgaaatccct    1740
tccacagacg tcactgataa aaccggtcgg gaacatctct cggtctatgc tgtggtggtg    1800
attgcgtctg tggtgggatt tgccttttg gtaatgctgt ttctgcttaa gttggcaaga    1860
cactccaagt tggcatgaa agatttctca tggtttggat ttgggaaagt aaaatcaaga    1920
caaggtgttg gcccagcctc cgttatcagc aatgatgatg actctgccag cccactccat    1980
cacatctcca atgggagtaa cactccatct tcttcggaag gtggcccaga tgctgtcatt    2040
attggaatga ccaagatccc tgtcattgaa atccccagt actttggcat caccaacagt     2100
cagctcaagc cagacacatt tgttcagcac atcaagcgac ataacattgt tctgaaaagg    2160
gagctaggcg aaggagcctt tggaaaagt ttcctagctg aatgctataa cctctgtcct    2220
gagcaggaca agatcttggt ggcagtgaag accctgaagg atgccagtga caatgcacgc   2280
aaggacttcc accgtgaggc cgagctcctg accaacctcc agcatgagca catcgtcaag   2340
ttctatggcg tctgcgtgga gggcgacccc ctcatcatgg tctttgagta catgaagcat   2400
ggggacctca caagttcct caggacacac ggccctgatg ccgtgctgat ggctgagggc    2460
aacccgccca cggaactgac gcagtcgcag atgctgcata tagcccagca gatcgccgcg   2520
ggcatggtct acctggcgtc ccagcacttc gtgcaccgcg atttggccac caggaactgc   2580
ctggtcgggg agaacttgct ggtgaaaatc ggggactttg gatgtcccg ggacgtgtac   2640 agcactgact actacaggt cggtggccac acaatgctgc ccattcgctg gatgcctcca   2700
gagagcatca tgtacaggaa attcacgacg gaaagcgacg tctggagcct ggggtcgtg    2760 ttgtgggaga ttttcaccta tggcaaacag ccctggtacc agctgtcaaa caatgaggtg    2820
atagagtgta tcactcaggg ccgagtcctg cagcgacccc gcacgtgccc ccaggaggtg    2880
tatgagctga tgctggggtg ctggcagcga gagcccaca tgaggaagaa catcaagggc    2940
atccataccc tccttcagaa cttggccaag gcatctccgg tctacctgga cattctaggc    3000
tag                                                                   3003
```

<210> SEQ ID NO 6
<211> LENGTH: 1000
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Met Glu Glu Leu Ile Val Glu Leu Arg Leu Phe Leu Glu Leu Leu Asp
1               5                   10                  15

His Glu Tyr Leu Thr Ser Thr Val Arg Glu Lys Lys Ala Val Ile Thr
            20                  25                  30
```

```
Asn Ile Leu Leu Arg Ile Gln Ser Ser Lys Gly Phe Asp Val Lys Asp
         35                  40                  45

His Ala Gln Lys Gln Glu Thr Ala Asn Ser Leu Pro Ala Pro Pro Gln
 50                  55                  60

Met Pro Leu Pro Glu Ile Pro Gln Pro Trp Leu Pro Pro Asp Ser Gly
 65                  70                  75                  80

Pro Pro Pro Leu Pro Thr Ser Ser Leu Pro Glu Gly Tyr Tyr Glu Glu
                 85                  90                  95

Ala Val Pro Leu Ser Pro Gly Lys Ala Pro Glu Tyr Ile Thr Ser Asn
                100                 105                 110

Tyr Asp Ser Asp Ala Met Ser Ser Tyr Ser Tyr Asp Glu Glu
                115                 120                 125

Glu Glu Asp Gly Lys Gly Lys Lys Thr Arg His Gln Trp Pro Ser Glu
        130                 135                 140

Glu Ala Ser Met Asp Leu Val Lys Asp Ala Lys Ile Cys Ala Phe Leu
145                 150                 155                 160

Leu Arg Lys Lys Arg Phe Gly Gln Trp Thr Lys Leu Leu Cys Val Ile
                165                 170                 175

Lys Asp Thr Lys Leu Leu Cys Tyr Lys Ser Ser Lys Asp Gln Gln Pro
                180                 185                 190

Gln Met Glu Leu Pro Leu Gln Gly Cys Asn Ile Thr Tyr Ile Pro Lys
        195                 200                 205

Asp Ser Lys Lys Lys His Glu Leu Lys Ile Thr Gln Gln Gly Thr
    210                 215                 220

Asp Pro Leu Val Leu Ala Val Gln Ser Lys Glu Gln Ala Glu Gln Trp
225                 230                 235                 240

Leu Lys Val Ile Lys Glu Ala Tyr Ser Gly Cys Ser Gly Pro Val Asp
                245                 250                 255

Ser Glu Cys Pro Pro Pro Ser Ser Pro Val His Lys Ala Glu Leu
            260                 265                 270

Glu Lys Lys Leu Ser Ser Glu Arg Pro Ser Ser Asp Gly Glu Gly Val
        275                 280                 285

Val Glu Asn Gly Ile Thr Thr Cys Asn Gly Lys Glu Gln Val Lys Arg
290                 295                 300

Lys Lys Ser Ser Lys Ser Glu Ala Lys Gly Thr Val Ser Lys Val Thr
305                 310                 315                 320

Gly Lys Lys Ile Thr Lys Ile Ile Ser Leu Gly Lys Lys Pro Ser
                325                 330                 335

Thr Asp Glu Gln Thr Ser Ser Ala Glu Asp Val Pro Thr Cys Gly
        340                 345                 350

Tyr Leu Asn Val Leu Ser Asn Ser Arg Trp Arg Glu Arg Trp Cys Arg
        355                 360                 365

Val Lys Asp Asn Lys Leu Ile Phe His Lys Asp Arg Thr Asp Leu Lys
    370                 375                 380

Thr His Ile Val Ser Ile Pro Leu Arg Gly Cys Glu Val Ile Pro Gly
385                 390                 395                 400

Leu Asp Ser Lys His Pro Leu Thr Phe Arg Leu Leu Arg Asn Gly Gln
                405                 410                 415

Glu Val Ala Val Leu Glu Ala Ser Ser Ser Glu Asp Met Gly Arg Trp
            420                 425                 430

Ile Gly Ile Leu Leu Ala Glu Thr Gly Ser Ser Thr Asp Pro Glu Ala
                435                 440                 445
```

```
Leu His Tyr Asp Tyr Ile Asp Val Glu Met Ser Ala Ser Val Ile Gln
450                 455                 460

Thr Ala Lys Gln Thr Phe Cys Phe Met Asn Arg Arg Val Ile Ser Ala
465                 470                 475                 480

Asn Pro Tyr Leu Gly Gly Thr Ser Asn Gly Tyr Ala His Pro Ser Gly
                    485                 490                 495

Thr Ala Leu His Tyr Asp Asp Val Pro Cys Ile Asn Gly Ser Leu Lys
                500                 505                 510

Gly Lys Lys Pro Pro Val Ala Ser Asn Gly Val Thr Gly Lys Gly Lys
            515                 520                 525

Thr Leu Ser Ser Gln Pro Lys Lys Ala Asp Pro Ala Ala Val Val Lys
530                 535                 540

Arg Thr Gly Ser Ser Ala Asn Pro Asn Tyr Pro Asp Val Ile Tyr Glu
545                 550                 555                 560

Asp Tyr Gly Thr Ala Ala Asn Asp Ile Gly Asp Thr Thr Asn Arg Ser
                565                 570                 575

Asn Glu Ile Pro Ser Thr Asp Val Thr Asp Lys Thr Gly Arg Glu His
            580                 585                 590

Leu Ser Val Tyr Ala Val Val Ile Ala Ser Val Val Gly Phe Cys
        595                 600                 605

Leu Leu Val Met Leu Phe Leu Leu Lys Leu Ala Arg His Ser Lys Phe
610                 615                 620

Gly Met Lys Asp Phe Ser Trp Phe Gly Phe Gly Lys Val Lys Ser Arg
625                 630                 635                 640

Gln Gly Val Gly Pro Ala Ser Val Ile Ser Asn Asp Asp Ser Ala
                645                 650                 655

Ser Pro Leu His His Ile Ser Asn Gly Ser Asn Thr Pro Ser Ser Ser
            660                 665                 670

Glu Gly Gly Pro Asp Ala Val Ile Ile Gly Met Thr Lys Ile Pro Val
        675                 680                 685

Ile Glu Asn Pro Gln Tyr Phe Gly Ile Thr Asn Ser Gln Leu Lys Pro
        690                 695                 700

Asp Thr Phe Val Gln His Ile Lys Arg His Asn Ile Val Leu Lys Arg
705                 710                 715                 720

Glu Leu Gly Glu Gly Ala Phe Gly Lys Val Phe Leu Ala Glu Cys Tyr
                725                 730                 735

Asn Leu Cys Pro Glu Gln Asp Lys Ile Leu Val Ala Val Lys Thr Leu
            740                 745                 750

Lys Asp Ala Ser Asp Asn Ala Arg Lys Asp Phe His Arg Glu Ala Glu
        755                 760                 765

Leu Leu Thr Asn Leu Gln His Glu His Ile Val Lys Phe Tyr Gly Val
770                 775                 780

Cys Val Glu Gly Asp Pro Leu Ile Met Val Phe Glu Tyr Met Lys His
785                 790                 795                 800

Gly Asp Leu Asn Lys Phe Leu Arg Ala His Gly Pro Asp Ala Val Leu
                805                 810                 815

Met Ala Glu Gly Asn Pro Pro Thr Glu Leu Thr Gln Ser Gln Met Leu
            820                 825                 830

His Ile Ala Gln Gln Ile Ala Ala Gly Met Val Tyr Leu Ala Ser Gln
        835                 840                 845

His Phe Val His Arg Asp Leu Ala Thr Arg Asn Cys Leu Val Gly Glu
850                 855                 860

Asn Leu Leu Val Lys Ile Gly Asp Phe Gly Met Ser Arg Asp Val Tyr
```

```
                865                 870                 875                 880
Ser Thr Asp Tyr Tyr Arg Val Gly Gly His Thr Met Leu Pro Ile Arg
                        885                 890                 895
Trp Met Pro Pro Glu Ser Ile Met Tyr Arg Lys Phe Thr Thr Glu Ser
                900                 905                 910
Asp Val Trp Ser Leu Gly Val Val Leu Trp Glu Ile Phe Thr Tyr Gly
            915                 920                 925
Lys Gln Pro Trp Tyr Gln Leu Ser Asn Asn Glu Val Ile Glu Cys Ile
        930                 935                 940
Thr Gln Gly Arg Val Leu Gln Arg Pro Arg Thr Cys Pro Gln Glu Val
945                 950                 955                 960
Tyr Glu Leu Met Leu Gly Cys Trp Gln Arg Glu Pro His Met Arg Lys
                965                 970                 975
Asn Ile Lys Gly Ile His Thr Leu Leu Gln Asn Leu Ala Lys Ala Ser
            980                 985                 990
Pro Val Tyr Leu Asp Ile Leu Gly
        995                 1000
```

<210> SEQ ID NO 7
<211> LENGTH: 1314
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 7

```
atgaacagtg gcggcggcct cccgcccccc tcggccgccg cctccccttc ctcctcctcg      60
ctggcggcgg cggtggcggt ggtggccccg ccggggcgtcg gggtgtccc cggcggggcg     120
gcggtaggag tgaagctgaa gtactgccgc tactacgcta aggataagac ttgcttctac     180
ggggaggagt gtcagttcct gcatgaggac cctgccgccg ggctgccccc gggcctcggc     240
ctccatagca acagcgtccc cctggctctg ctggtgcac ccgtggccgg cttccgccg       300
ggagccgtcg cgggcggggg agctgggccg ccccccgggc caagaagcc ggacctgggg      360
gacccgggga ccggagccgc agccggcgga ggaggcagta gcggggact cgatggaccg     420
cggctggcaa ttgttcagca catcaagcga cataacattg ttctgaaaag ggagctaggc    480
gaaggagcct ttggaaaagt gttcctagct gaatgctata acctctgtcc tgagcaggac   540
aagatcttgg tggcagtgaa gaccctgaag gatgccagtg acaatgcacg caaggacttc    600
caccgtgagg ccgagctcct gaccaacctc agcatgagc acatcgtcaa gttctatggc    660
gtctgcgtgg agggcgaccc cctcatcatg gtctttgagt acatgaagca tgggaccctc    720
aacaagttcc tcagggcaca cggccctgat gccgtgctga tggctgaggg caacccgccc    780
acggaactga cgcagtcgca gatgctgcat atagcccagc agatcgccgc gggcatggtc    840
tacctggcgt cccagcactt cgtgcaccgc gatttggcca ccaggaactg cctggtcggg   900
gagaacttgc tggtgaaaat cggggacttt gggatgtccc gggacgtgta cagcactgac    960
tactacaggg tcggtggcca cacaatgctg cccattcgct ggatgcctcc agagagcatc   1020
atgtacagga aattcacgac ggaaagcgac gtctggagcc tggggtcgt gttgtgggag   1080
attttcacct atggcaaaca gccctggtac cagctgtcaa caatgaggt gatagagtgt    1140
atcactcagg gccgagtcct gcagcgaccc cgcacgtgcc cccaggaggt gtatgagctg   1200
atgctggggt gctggcagcg agagcccac atgaggaaga acatcaaggg catccatacc   1260
```
ctccttcaga acttggccaa ggcatctccg gtctacctgg acattctagg ctag    1314

<210> SEQ ID NO 8
<211> LENGTH: 437
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Met Asn Ser Gly Gly Gly Leu Pro Pro Ser Ala Ala Ala Ser Pro
1               5                   10                  15

Ser Ser Ser Ser Leu Ala Ala Val Ala Val Val Ala Pro Pro Gly
                20                  25                  30

Val Gly Gly Val Pro Gly Gly Ala Ala Val Gly Val Lys Leu Lys Tyr
            35                  40                  45

Cys Arg Tyr Tyr Ala Lys Asp Lys Thr Cys Phe Tyr Gly Glu Glu Cys
    50                  55                  60

Gln Phe Leu His Glu Asp Pro Ala Ala Gly Ala Ala Pro Gly Leu Gly
65                  70                  75                  80

Leu His Ser Asn Ser Val Pro Leu Ala Leu Ala Gly Ala Pro Val Ala
                85                  90                  95

Gly Phe Pro Pro Gly Ala Val Ala Gly Gly Ala Gly Pro Pro Pro
            100                 105                 110

Gly Pro Lys Lys Pro Asp Leu Gly Asp Pro Gly Thr Gly Ala Ala Ala
        115                 120                 125

Gly Gly Gly Gly Ser Ser Gly Gly Leu Asp Gly Pro Arg Leu Ala Ile
    130                 135                 140

Val Gln His Ile Lys Arg His Asn Ile Val Leu Lys Arg Glu Leu Gly
145                 150                 155                 160

Glu Gly Ala Phe Gly Lys Val Phe Leu Ala Glu Cys Tyr Asn Leu Cys
                165                 170                 175

Pro Glu Gln Asp Lys Ile Leu Val Ala Val Lys Thr Leu Lys Asp Ala
            180                 185                 190

Ser Asp Asn Ala Arg Lys Asp Phe His Arg Glu Ala Glu Leu Leu Thr
        195                 200                 205

Asn Leu Gln His Glu His Ile Val Lys Phe Tyr Gly Val Cys Val Glu
    210                 215                 220

Gly Asp Pro Leu Ile Met Val Phe Glu Tyr Met Lys His Gly Asp Leu
225                 230                 235                 240

Asn Lys Phe Leu Arg Ala His Gly Pro Asp Ala Val Leu Met Ala Glu
                245                 250                 255

Gly Asn Pro Pro Thr Glu Leu Thr Gln Ser Gln Met Leu His Ile Ala
            260                 265                 270

Gln Gln Ile Ala Ala Gly Met Val Tyr Leu Ala Ser Gln His Phe Val
        275                 280                 285

His Arg Asp Leu Ala Thr Arg Asn Cys Leu Val Gly Glu Asn Leu Leu
    290                 295                 300

Val Lys Ile Gly Asp Phe Gly Met Ser Arg Asp Val Tyr Ser Thr Asp
305                 310                 315                 320

Tyr Tyr Arg Val Gly Gly His Thr Met Leu Pro Ile Arg Trp Met Pro
                325                 330                 335

Pro Glu Ser Ile Met Tyr Arg Lys Phe Thr Thr Glu Ser Asp Val Trp
```

-continued

```
                340                 345                 350
Ser Leu Gly Val Val Leu Trp Glu Ile Phe Thr Tyr Gly Lys Gln Pro
            355                 360                 365

Trp Tyr Gln Leu Ser Asn Asn Glu Val Ile Glu Cys Ile Thr Gln Gly
        370                 375                 380

Arg Val Leu Gln Arg Pro Arg Thr Cys Pro Gln Glu Val Tyr Glu Leu
385                 390                 395                 400

Met Leu Gly Cys Trp Gln Arg Glu Pro His Met Arg Lys Asn Ile Lys
            405                 410                 415

Gly Ile His Thr Leu Leu Gln Asn Leu Ala Lys Ala Ser Pro Val Tyr
            420                 425                 430

Leu Asp Ile Leu Gly
        435
```